(12) United States Patent
Rioux et al.

(10) Patent No.: US 10,578,415 B2
(45) Date of Patent: *Mar. 3, 2020

(54) SURGICAL DEPTH INSTRUMENT HAVING NEUROMONITORING CAPABILITIES

(71) Applicant: EDGE SURGICAL, INC., Chicago, IL (US)

(72) Inventors: Robert F. Rioux, Ashland, MA (US); Christopher Wilson, Chicago, IL (US); Victor Simoes, Northport, NY (US); Tyler Wanke, Chicago, IL (US)

(73) Assignee: EDGE SURGICAL, INC., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/162,974

(22) Filed: Oct. 17, 2018

(65) Prior Publication Data

US 2019/0049227 A1 Feb. 14, 2019

Related U.S. Application Data

(63) Continuation of application No. 15/801,824, filed on Nov. 2, 2017, now Pat. No. 10,132,607.

(Continued)

(51) Int. Cl.
*G01B 3/28* (2006.01)
*G01B 3/20* (2006.01)
(Continued)

(52) U.S. Cl.
CPC ............... *G01B 3/28* (2013.01); *A61B 17/17* (2013.01); *A61B 90/06* (2016.02); *B23B 49/00* (2013.01);
(Continued)

(58) Field of Classification Search
CPC ........... G01B 3/28; A61B 17/17; A61B 90/06; B23B 49/00
(Continued)

(56) References Cited

U.S. PATENT DOCUMENTS 2,650,435 A * 9/1953 Kidd .................. G01B 3/28
33/836
2,689,408 A 9/1954 Cornell et al.
(Continued)

FOREIGN PATENT DOCUMENTS

WO 2005027745 A1 3/2005

OTHER PUBLICATIONS

Checkpoint Surgical, "A Signifcant Advance in Neuroprotective Surgery", Checkpoint Surgical Inc., 2014 (6 Pages).
(Continued)

*Primary Examiner* — Christopher W Fulton
(74) *Attorney, Agent, or Firm* — Brown Rudnick LLP

(57) ABSTRACT

A device configured to provide a faster and more accurate measurement of depths of holes for placement of bone screws and fastener for bone implant fixation procedures. The device includes a combination of a bone probe for physical examination of a hole drilled in a bone and a depth gauge member for determining a depth of the hole and providing digital measurement of the depth via a display on the instrument and/or via a wireless exchange of measurement data to a remote computing device, such as a tablet or smartphone. The device may further be connected to a separate neuromonitoring device and be used for nerve sensing and/or nerve stimulation by way of the bone probe. For example, the bone probe may include a conductive material such that the distal probe tip acts as an extension of the neuromonitoring device and may be used to sense and/or stimulate nerves.

20 Claims, 13 Drawing Sheets

Related U.S. Application Data

(60) Provisional application No. 62/554,470, filed on Sep. 5, 2017, provisional application No. 62/471,873, filed on Mar. 15, 2017, provisional application No. 62/417,046, filed on Nov. 3, 2016.

(51) Int. Cl.
| | |
|---|---|
| *A61B 90/00* | (2016.01) |
| *G01B 7/16* | (2006.01) |
| *A61B 17/17* | (2006.01) |
| *B23B 49/00* | (2006.01) |
| *A61B 5/107* | (2006.01) |

(52) U.S. Cl.
CPC ............... *G01B 3/205* (2013.01); *G01B 7/16* (2013.01); *A61B 5/107* (2013.01); *A61B 2090/062* (2016.02); *A61B 2090/067* (2016.02); *A61B 2090/0807* (2016.02); *G01B 2210/58* (2013.01)

(58) Field of Classification Search
USPC .......................................................... 33/512
See application file for complete search history.

(56) References Cited

U.S. PATENT DOCUMENTS

| | | | |
|---|---|---|---|
| 3,058,225 A | 10/1962 | Ward | |
| 5,013,318 A | 5/1991 | Spranza, III | |
| 5,037,426 A * | 8/1991 | Goble ................ | A61B 17/8645 606/96 |
| 5,758,433 A * | 6/1998 | Alberts .................... | G01B 3/28 33/542 |
| 5,772,661 A | 6/1998 | Michelson | |
| 5,860,973 A | 1/1999 | Michelson | |
| 5,928,243 A | 7/1999 | Guyer | |
| 6,235,028 B1 | 5/2001 | Brumfield et al. | |
| 6,428,542 B1 | 8/2002 | Michelson | |
| 6,530,929 B1 | 3/2003 | Justis et al. | |
| 6,592,586 B1 | 7/2003 | Michelson | |
| 6,916,320 B2 | 7/2005 | Michelson | |
| 6,936,050 B2 | 8/2005 | Michelson | |
| 6,936,051 B2 | 8/2005 | Michelson | |
| 6,945,933 B2 | 9/2005 | Branch et al. | |
| 6,969,390 B2 | 11/2005 | Michelson | |
| 7,008,422 B2 | 3/2006 | Foley et al. | |
| 7,165,336 B2 | 1/2007 | Kim | |
| 7,444,756 B2 | 11/2008 | Kim | |
| 7,493,703 B2 | 2/2009 | Kim et al. | |
| 7,607,238 B2 | 10/2009 | Kim et al. | |
| 7,676,943 B2 | 3/2010 | Kim et al. | |
| 7,685,735 B2 | 3/2010 | Kim | |
| 7,730,629 B2 | 6/2010 | Kim | |
| 7,878,981 B2 | 2/2011 | Strother et al. | |
| 7,895,762 B2 | 3/2011 | Kim et al. | |
| 7,895,767 B2 | 3/2011 | Harshbarger et al. | |
| 7,896,815 B2 | 3/2011 | Thrope et al. | |
| 8,172,768 B2 | 5/2012 | Strother et al. | |
| 8,221,427 B2 | 7/2012 | Roh | |
| 8,500,652 B2 | 8/2013 | Strother et al. | |
| 10,132,607 B2 * | 11/2018 | Rioux .................... | A61B 17/17 |
| 10,151,570 B2 * | 12/2018 | Jacobs .................. | A61B 17/17 |
| 2002/0104230 A1 | 8/2002 | White | |
| 2003/0233098 A1 * | 12/2003 | Markworth ............ | A61B 17/17 606/96 |
| 2005/0066535 A1 | 3/2005 | Rupp et al. | |
| 2006/0224161 A1 | 10/2006 | Bhattacharyya | |
| 2007/0088366 A1 | 4/2007 | Fernandez | |
| 2008/0104855 A1 | 5/2008 | Kim et al. | |
| 2009/0005786 A1 | 1/2009 | Prien et al. | |
| 2009/0157088 A1 | 6/2009 | Mengato | |
| 2010/0198227 A1 | 8/2010 | Kim et al. | |
| 2011/0054346 A1 | 3/2011 | Hausman et al. | |
| 2011/0060238 A1 | 3/2011 | Hausman et al. | |
| 2011/0060243 A1 | 3/2011 | Hausman et al. | |
| 2012/0296442 A1 | 11/2012 | Hausman | |
| 2013/0096565 A1 | 4/2013 | Fritzinger | |
| 2013/0172897 A1 | 7/2013 | Dell'Oca et al. | |
| 2013/0245490 A1 | 9/2013 | Strother et al. | |
| 2013/0296733 A1 | 11/2013 | Strother et al. | |
| 2014/0073985 A1 | 3/2014 | Sakai et al. | |
| 2014/0296861 A1 | 10/2014 | McCarthy et al. | |
| 2014/0371622 A1 | 12/2014 | Hausman et al. | |
| 2015/0133944 A1 | 5/2015 | Kortenbach | |
| 2018/0256277 A1 | 9/2018 | Garvey et al. | |

OTHER PUBLICATIONS

Checkpoint Surgical, "Nerve Repair: Manual", Checkpoint Surgical Inc., 2016 (44 Pages).
Checkpoint Surgical, "The Next Generation in Neuroprotective Surgical Technology", Checkpoint Surgical Inc., 2014 (6 Pages).
International Search Report and Written Opinion dated May 24, 2018 for International Application No. PCT/US2017/059709 (13 Pages).
International Search Report and Written Opinion dated May 24, 2018 for International Application No. PCT/US2017/059714 (13 Pages).
Medartis "Ordering Catalog", Medartis AG, 2017 (100 Pages).
Medartis "Surgical Technique—Step by Step, APTUS Hand", Medartis AG, 2012 (20 Pages).
Medtronic, "Nim-Spine System", Medtronic Sofamor Danek, 2005 (4 Pages).
Surgionix, "Surgical Technique Guide", Surgionix Ltd., 2013 (12 Pages).

\* cited by examiner

SURGICAL DEPTH INSTRUMENT HAVING NEUROMONITORING CAPABILITIES

CROSS-REFERENCE TO RELATED APPLICATIONS

This application is a continuation of U.S. Nonprovisional Application No. 15/801,824, filed Nov. 2, 2017, now U.S. Pat. No. 10,132,607, which claims the benefit of, and priority to, U.S. Provisional Application No. 62/417,046, filed Nov. 3, 2016, U.S. Provisional Application No. 62/471,873, filed Mar. 15, 2017 and U.S. Provisional Application No. 62/554,470, filed Sep. 5, 2017, the contents of each of which are hereby incorporated by reference herein in their entireties.

FIELD

The present disclosure relates generally to medical devices, and, more particularly, to a measuring instrument for use in a bone implant fixation procedure, the measuring instrument including a combination of a bone probe allowing for physical examination of a hole drilled in a bone and a depth gauge member for determining a depth of the hole and providing a digital measurement of the depth.

BACKGROUND

Orthopedics is a medical specialty concerned with the correction of deformities or functional impairments of the skeletal system, especially the extremities and the spine, and associated structures, such as muscles and ligaments. Some orthopedic surgical procedures require surgeons to secure a device to one or more bones of a patient. For example, in some procedures, the surgeon may span and secures one or more bones, or pieces of a single bone, using a bone plate and one or more fasteners, such as screws. Other bone-related surgical procedures, however, may not require a bone plate and may instead solely rely on the use of one or more screws (e.g., securing a transplanted tendon).

In such bone-related surgical procedures, before an implant or plate, or simply the screw itself, can be attached to bone, an opening is typically drilled into the bone to accommodate the screw. With a hole in place, the surgeon can more easily select a screw of the appropriate length. However, selecting a screw of appropriate length is critical. For example, if the selected screw is too long, the distal end of the screw may pass through the end of the drilled hole and cause damage to the bone and/or protrude entirely through the bone, which can have deleterious effects, such as damage to surrounding tissue and/or pain and discomfort, or more serious complications, for the patient. For example, in some instances, the bone may abut against soft tissues that may be harmed if the screw is too long and may result in irritation of or damage to the soft parts. Additionally, a screw that protrudes through the bone may be tactilely felt by the patient, may prevent soft tissues (e.g., tendons, ligaments, or muscles) from moving over the bone surface as intended, or may even pierce the skin, which can lead to serious infection and complications.

The selection of an appropriate length screw is particularly important in spinal fixation procedures, such as lumbar sacral fusion and the correction of spinal deformities such as scoliotic curves. As an example, a screw mounted in the pedicle portion of the human spine should not extend to a point where the screw contacts the spinal cord itself, an event that can cause irreparable nervous system damage including paralysis. Accordingly, the determination of a length of the hole is important for choosing the appropriate length screw.

During drilling, the surgeon is typically capable of recognizing the resistance on the drill in order to determine when the drill has penetrated through the bone. Because the simple act of drilling does not provide an exact measurement of the depth of the bone itself, a depth gauge is commonly employed for directly measuring the depth of the hole from the top, drilling side to the bottom, opposite side of the hole.

Currently, many designs are known and utilized for measuring the depth of a hole or bore in a portion of a bone. Generally speaking, these designs utilize a central probe member having a barb at a distal end, and a sleeve or channel member. The probe member is inserted into the pilot hole while the surgeon attempts to find the surface with the barb. More specifically, the probe member is inserted to a depth greater than the depth of the pilot hole so that the barb is beyond the opposite side, at which point the surgeon finds the surface by hooking the barb to the opposite side.

The probe member is received in the sleeve or channel member and may reciprocate relative thereto. The channel member has graduated markings along a portion of its length, typically in inches and/or millimeters. A marker is laterally secured to the probe member such that, as the probe member shifts relative to the channel member, the marker indicates the relative shift between the probe member and the channel member. Accordingly, once the probe member has been secured to the opposite side of the bone, the channel member is shifted relative to the probe member and toward the bone until the channel member abuts the surface of the bone. The depth gauge is then read by examining graduated markings indicated by the probe member marker.

A number of problems are experienced with this depth gauge. As an initial point, the components are typically made with surgical-grade stainless steel, and the graduated markings are embossed therein. Therefore, the brightness of the operating room lights on the highly reflective surface can make the markings difficult to read. The markings are commonly in small increments, such as millimeters, and surgeons often have trouble differentiating between the markings, or noting partial increments. Reading these gauges, then, often requires carefully holding the depth gauge as the reading is taken, and a surgeon's effort to closely examine the reading may result in a loss of securement or purchase of the barb on the bone, thus necessitating a re-measurement and a loss of time.

Furthermore, proper reading of the markings requires a surgeon's eyes to be properly aligned with the markings. That is, a proper view of the measurement requires the surgeon to view the gauge from a lateral point of view so that the view of the probe marker aligned with the graduated markings is proper not distorted by the surgeon's elevated, standing perspective. Therefore, it is often necessary for the surgeon to bend over while using these gauges to view an accurate reading. If the depth gauge is tilted in order to make the reading, the sleeve will shift relative to the probe, thus making the measurement inaccurate and possibly causing the barb to become unsecured, as described above. In addition, removal of the depth gauge often causes the measurement to be lost. As the bone is essentially clamped, by light pressure, between the distal end of the channel member and the distal barb of the probe member, it is often necessary to retract the channel member from the bone surface in order to extract the probe from the pilot hole.

SUMMARY

The present disclosure is a medical device for use in a bone implant fixation procedure. The device is configured to provide a faster and more accurate measure of depth. In particular, the device includes a combination of a bone probe allowing for physical examination of a hole drilled in a bone and a depth gauge member for determining a depth of the hole and providing a digital measurement of the depth. Accordingly, the device of the present disclosure is capable of digitally measuring the depth of an opening in a bone during the same surgical step that a surgeon probes and inspects the interior of the opening.

During a bone-related procedure involving placement of a screw, or other fastener, it may be desirable to determine whether drilling of the hole resulted in any cracks or openings, either along an interior side wall of the hole or at the base of the hole. Ensuring the integrity of the drilled hole is important because unintended cracks, openings, or irregularities can increase the risk that the screw will either not securely attach itself within the hole or may result in chipping or fragmenting of bone during fastening of the screw within the hole. It is generally not possible for a surgeon to visual examine the integrity of the drilled hole due to a limited field of view within the hole (drilled holes can be relatively small in width, such as 5 mm or less in some instances).

The device of the present disclosure includes a bone probe that allows for a surgeon to feel the interior side walls and base of the hole to locate any cracks or other unintended openings or irregularities along the interior of the hole. The bone probe generally includes an elongated shaft slidably mounted within a body of the device serving as a handle adapted for manual manipulation. The elongated shaft of the probe includes a distal end configured to extend from the body of the device during use. The distal end includes a probing tip for contacting an interior portion of the hole. At least a portion of the elongated shaft may be substantially flexible or semi-rigid to provide a proper "feel" to the surgeon during examination of the hole in the bone. For example, the shaft of the bone probe may be substantially non-elastic such that the surgeon can apply pressure against the interior wall of the hole to feel for irregularities or the base of the hole via tactile feedback provided by the shaft. In some embodiments, the shaft may be tapered such that the shaft narrows in width in a direction towards the probing distal tip. In this manner, the flexibility of the shaft may increase along the shaft in a direction toward the probing tip.

The probing tip may include at least a first portion having a shape or contour that aids the surgeon in detecting surface irregularities (e.g., cracks, crevices, openings, etc.) on the interior surface of the hole. For example, in some embodiments the first portion may have a substantially arcuate or curved shape. The arcuate or curved portion may also aid the surgeon in locating the bottom or base of the hole so as to allow for the depth of the hole to be measured via the depth gauge member. The arcuate or curved shape of the first portion of the probing tip may generally lessen risk of tissue irritation that may otherwise occur along the interior surface of the hole, which is usually soft and easily penetrable with less curved and more abrupt surfaces (with sharp or distinct edges). In some embodiments, the first portion may have a general spherical shape. In other embodiments, the first portion may be substantially planar with rounded edges.

The probing tip may also include a second portion positioned opposite the first portion, wherein the second portion includes an engagement surface configured to pierce or otherwise establish purchase with an interior of the hole upon application of sufficient force from the surgeon. In particular, upon locating the base or bottom of the hole, the surgeon may then apply sufficient force upon the shaft of the bone probe so that the engagement surface of the probing tip engages and establishes purchase with a sidewall immediately adjacent the base of the hole. Upon establishing engagement, the medical device may be stabilized in position, at which point, the depth gauge member can be used for measuring the depth of the hole. In some embodiments, the engagement surface may include surface texturing to enhance friction between the engagement surface and a portion of bone. For example, in some procedures in which a plate or implants is to be secured with screws through a bicortical drill hole, the probing tip may extend entirely through the hole (from one side of the bone to the other), at which point the surgeon may pull the bone probe back towards the hole such that the engagement surface of the second portion of the probing tip establishes purchase with one side of the bone, and the surface texturing enhances friction between the engagement surface and bone to reduce risk of slippage.

The depth gauge member generally includes a hollow elongated body slidably mounted within the body of the device and includes a distal end configured to extend from the first end of the body during use. The hollow elongated body includes a lumen in which at least a portion of the bone probe shaft is received within such that the bone probe and depth gauge member are independently slidable relative to one another and the body of the device.

The device further includes at least one sensor configured to generate an electronic signal indicative of a depth of the hole as a result of sensing a distance between the first end of the device body and the distal end of the depth gauge member. For example, in one embodiment, upon establishing purchase with a bottom interior surface of the hole via the probing tip, a surgeon need only move the device handle (i.e., device body) in a direction towards the bone such that the first end of the handle contacts a surface of the bone proximate the open end of the hole. The surgeon may then advance the depth gauge member towards hole, such that the distal end of the depth gauge member extends from the first end of the device handle and advances into the hole, sliding over the bone probe. While the bone probe is maintained in engagement with the bottom of the hole via the probing tip, the depth gauge member may be advanced in a direction towards the bottom of the hole until the distal end of the depth gauge member makes contact with the bottom of the hole. The bone probe essentially acts as a guide upon which the depth gauge member slide over when advancing to the bottom of the hole.

The sensor is configured to generate an electronic signal based on a distance between the first end of the body and the distal end of the depth gauge member, wherein the electronic signal is indicative of at least a depth of the hole. In particular, the sensor may include inductive or capacitive elements or assemblies configured to sense the location of the distal end of the depth gauge member relative to the first end of the device body, and, as a result, generate an electronic signal representing the distance there between. Accordingly, the sensed distance between the first end of the device handle (when abutting the bone surface) and the distal end of the depth gauge member (when abutting the bottom of the hole) is the depth of the hole.

It should be noted that the device may include logic or allow for adjustment to the sensing capabilities so as to program the sensor to account for other variables when sensing the depth of the hole. For example, in some embodiments, certain procedures require fixing a plate or implant to the bone via screws. Accordingly, the screw length must not only be sufficient to fill the hole but also long enough to account for the thickness of a plate or implant through which it passes when engaging the hole. Accordingly, in some embodiments, the sensor may be programmed so as to account for the thickness of the plate or implant and will further include that thickness in the electronic signal produced, such that the electronic signal is indicative of the total depth that a corresponding screw length will need to cover, including the depth of the hole in the bone in addition to the thickness of the plate or implant through which the screw will pass through and the screw head will engage.

Furthermore, in some instances, first end of the device handle will be directly abutting a surface of the plate or implant, which is directly abutting the surface of the bone, when the surgeon is measuring the depth. Thus, in this case, the sensor is still able to sense a distance between the first end of the device handle and the distal end of the depth gauge member, which will provide an overall depth, rather than just a depth of the hole in the bone.

Accordingly, the digital sensing of the hole depth provides a much more accurate measurement than conventional analog depth gauges and also requiring very little, if any, input or interpretation from the surgeon. Accordingly, by providing a much more accurate measurement of a hole depth, the surgeon is able to select the correct length screw for any given hole so as to improve the chances of a successful surgery.

In some embodiments, the device may further include a display provided on the body and configured to visually provide a digital readout of a depth measurement of the hole based on the electronic signal from the sensor. In other embodiments, the device may be configured to wirelessly communicate and exchange data with a separate display or computing device, such as, for example, a monitor or panel display, a PC, a notebook, a tablet computer, a smartphone, or other wireless computing device.

Upon receiving the electronic signal from the sensor, the separate display or computing device may be configured to visually provide the depth measurement of the hole based on the electronic signal from the sensor. Furthermore, in some embodiments, the computing device may include a specific software application that may be directed to maintaining a record of the hole measurements and/or provide an interactive user interface in which multiple holes can be mapped to a particular plate or implant and the depth of each hole (including the thickness of the plate or implant) can be included and stored for records.

In some embodiments, the device may further include a sensor configured to sense strain of the bone probe shaft. In particular, the sensor may include a strain gauge or the like configured to determine a strain of the bone probe shaft, which may be useful for alerting the surgeon of an amount of resistance that the distal probing tip is encountering during probing of the interior of the hole. For example, while a surgeon may be able to "feel" the interior surface and further have a sense of when the probing tip actually makes contact with the bottom of the hole, the strain sensor may further generate an electronic signal based on a sensed strain of the shaft which may then be used to provide an audible and/or visual alert to the surgeon indicating that the probing tip is in fact positioned at the bottom of the hole. For example, the resistance encountered when the probing tip engages the bottom of the hole may have a certain strain value (i.e., above a certain threshold) which may be different than a resistance encountered with the sidewalls of the hole (which may have a softer, spongier tissue). Accordingly, the audible and/or visual alert may confirm to a surgeon whether they are in fact positioned at the bottom of the hole or if too much pressure is being placed against the interior surface such that they risk possibly inadvertently piercing the interior surface.

In some embodiments, the device may further be compatible with other medical devices so as to provide additional features, in additional bone probing and depth measurement. For example, in some embodiments, the bone probe shaft may include an electrically conductive material (e.g., a metal such as stainless steel, nitinol, or aluminum), wherein a portion of the bone probe shaft may be exposed, or otherwise accessible, along a portion of the device handle. In particular, the device handle may include an aperture, window, or the like, that provides access to an interior of the handle, particularly providing access to an exposed portion of the bone probe shaft. Thus, in some embodiments, an electrical current from a separate device may be supplied to the bone probe shaft via the access region (e.g., slide a working tip of an electrocautery device into the access region to make contact with bone probe shaft). As a result of being made from a conductive material, the bone probe shaft may carry the electrical current to the distal probe tip, which may then be used to deliver energy to a desired target (e.g., interior surface of hole of the bone) as a result of the electrical current applied thereto. Similarly, a separate nerve sensing/stimulation device may be coupled to the conductive bone probe shaft via the access region, such that the distal probe tip essentially acts as an extension to the nerve sensing/stimulation device and may be used to sense/stimulate nerves within the bone.

Yet still, in another embodiment, the handle may include a port in communication with a portion of the bone probe shaft. The port may provide access from an exterior of the handle to an interior of the handle and to the bone probe shaft. The port may be configured to receive and place an input connector of a second medical device, such as a neuromonitoring device, for nerve sensing and/or nerve stimulation, into electrical communication with the bone probe shaft, such that the bone probe shaft can be used to carry electrical signals to and from the input connector of the second medical device.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

Figure 1:
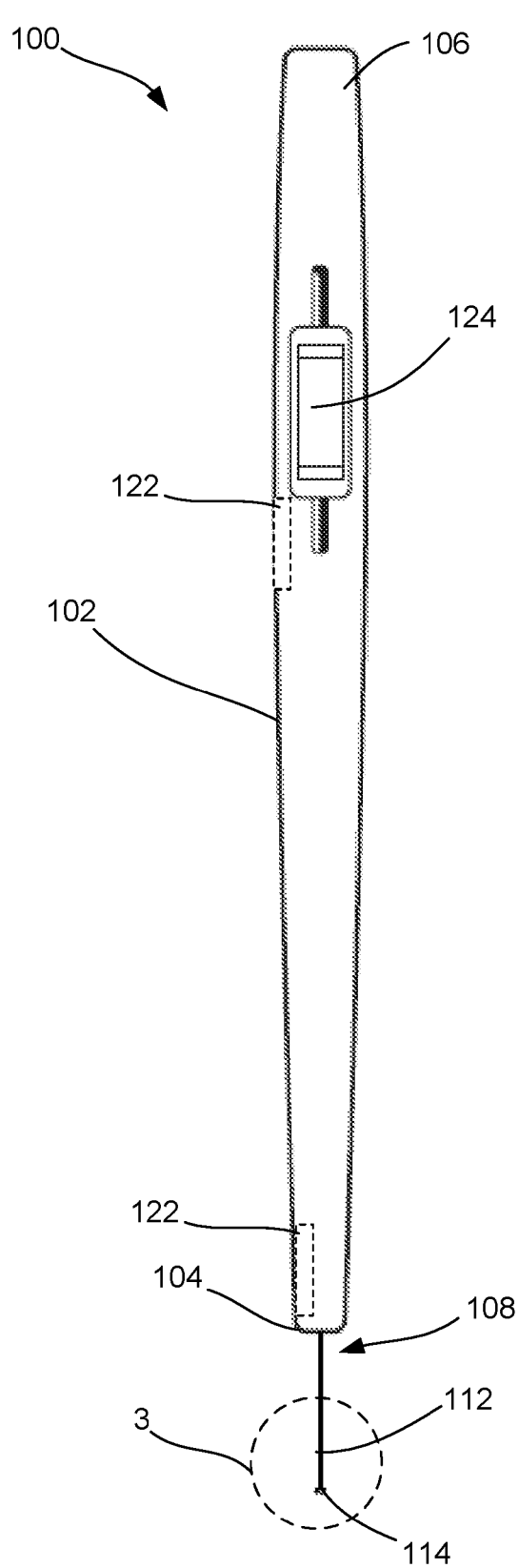
FIG. 1 is top view of one embodiment of a medical device consistent with the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present disclosure is generally directed to a medical device for use in a bone implant fixation procedure and configured to provide a faster and more accurate measure of depth. In particular, the device includes a combination of a bone probe allowing for physical examination of a hole drilled in a bone and a depth gauge member for determining a depth of the hole and providing a digital measurement of the depth. Accordingly, the device of the present disclosure is capable of digitally measuring the depth of an opening in a bone during the same surgical step that a surgeon probes and inspects the interior of the opening.

The device of the present disclosure includes a bone probe that allows for a surgeon to feel the interior side walls and base of the hole to locate any cracks or other unintended openings or irregularities along the interior of the hole. The bone probe generally includes an elongated shaft slidably mounted within a body of the device serving as a handle adapted for manual manipulation. The elongated shaft of the probe includes a distal end configured to extend from the body of the device during use. The distal end includes a probing tip for contacting an interior portion of the hole. At least a portion of the elongated shaft may be substantially flexible or semi-rigid to provide a proper "feel" to the surgeon during examination of the hole in the bone. For example, the shaft of the bone probe may be substantially non-elastic such that the surgeon can apply pressure against the interior wall of the hole to feel for irregularities or the base of the hole via tactile feedback provided by the shaft. In some embodiments, the shaft may be tapered such that the shaft narrows in width in a direction towards the probing distal tip. In this manner, the flexibility of the shaft may increase along the shaft in a direction toward the probing tip.

The probing tip may include at least a first portion having a shape or contour that aids the surgeon in detecting surface irregularities (e.g., cracks, crevices, openings, etc.) on the interior surface of the hole. For example, in some embodiments the first portion may have a substantially arcuate or curved shape. The arcuate or curved portion may also aid the surgeon in locating the bottom or base of the hole so as to allow for the depth of the hole to be measured via the depth gauge member. The arcuate or curved shape of the first portion of the probing tip may generally lessen risk of tissue irritation that may otherwise occur along the interior surface of the hole, which is usually soft and easily penetrable with less curved and more abrupt surfaces (with sharp or distinct edges). In some embodiments, the first portion may have a generally spherically shape. In other embodiments, the first portion may be substantially planar with rounded edges.

The probing tip may also include a second portion positioned opposite the first portion, wherein the second portion includes an engagement surface configured to pierce or otherwise establish purchase with an interior of the hole upon application of sufficient force from the surgeon. In particular, upon locating the base or bottom of the hole, the surgeon may then apply sufficient force upon the shaft of the bone probe so that the engagement surface of the probing tip engages and establishes purchase with a sidewall immediately adjacent the base of the hole. Upon establishing engagement, the medical device may be stabilized in position, at which point, the depth gauge member can be used for measuring the depth of the hole. In some embodiments, the engagement surface may include surface texturing to enhance friction between the engagement surface and a portion of bone. For example, in some procedures in which a plate or implants is to be secured with screws through a bicortical drill hole, the probing tip may extend entirely through the hole (from one side of the bone to the other), at which point the surgeon may pull the bone probe back towards the hole such that the engagement surface of the second portion of the probing tip establishes purchase with one side of the bone, and the surface texturing enhances friction between the engagement surface and bone to reduce risk of slippage.

The depth gauge member generally includes a hollow elongated body slidably mounted within the body of the device and includes a distal end configured to extend from the first end of the body during use. The hollow elongated body includes a lumen in which at least a portion of the bone probe shaft is received within such that the bone probe and depth gauge member are independently slidable relative to one another and the body of the device.

The device further includes at least one sensor configured to generate an electronic signal indicative of a depth of the hole as a result of sensing a distance between the first end of the device body and the distal end of the depth gauge member. For example, in one embodiment, upon establishing purchase with a bottom interior surface of the hole via the probing tip, a surgeon need only move the device handle (i.e., device body) in a direction towards the bone such that the first end of the handle contacts a surface of the bone proximate the open end of the hole or a surface of a plate or implant to be fixed to the bone. The surgeon may then advance the depth gauge member towards hole in the bone, such that the distal end of the depth gauge member extends from the first end of the device handle and advances into the hole, sliding over the bone probe. While the bone probe is maintained in engagement with the bottom of the hole via the probing tip, the depth gauge member may be advanced in a direction towards the bottom of the hole until the distal end of the depth gauge member makes contact with the bottom of the hole. The bone probe essentially acts as a guide upon which the depth gauge members slide over when advancing to the bottom of the hole.

The sensor is configured to generate an electronic signal based on a distance between the first end of the body and the distal end of the depth gauge member, wherein the electronic signal is indicative of at least a depth of the hole. In particular, the sensor may include inductive or capacitive elements or assemblies configured to sense the location of the distal end of the depth gauge member relative to the first end of the device body, and, as a result, generate an electronic signal representing the distance there between. Accordingly, the sensed distance between the first end of the device handle (when abutting the bone surface) and the distal end of the depth gauge member (when abutting the bottom of the hole) is the depth of the hole.

Accordingly, the digital sensing of the hole depth provides a much more accurate measurement than conventional analog depth gauges and also requiring very little, if any, input or interpretation from the surgeon. Accordingly, by providing a much more accurate measurement of a hole depth, the surgeon is able to select the correct length screw for any given hole so as to improve the chances of a successful surgery.

Figure 2:
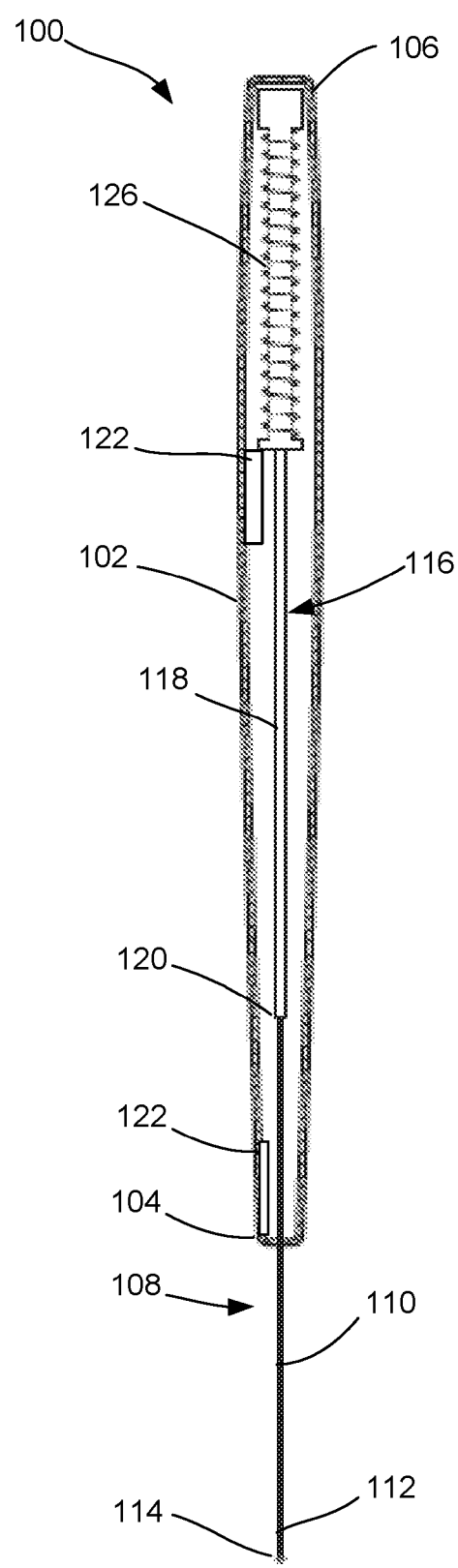
FIG. 2 is a cross-sectional view of the medical device of FIG. 1 illustrating the hollow interior of the handle and arrangement of the bone probe and depth gauge member relative to one another.

FIG. 1 is top view of one embodiment of a medical device 100 consistent with the present disclosure and FIG. 2 provides a cross-sectional view of the medical device 100. As shown, the medical device 100 includes a body 102 having a first end 104 and an opposing second end 106 and is generally hollow. The body 102 is configured as a handle and generally adapted for manual manipulation. Accordingly, the body will be referred to a "handle 102" hereinafter for ease of explanation.

The device 100 further includes a bone probe 108 slidably mounted within the handle 102. The bone probe 108 includes a shaft 110 having a distal end 112 configured to extend from, and retract towards, the first end 104 of the handle 102 during use, as will be described in greater detail herein. The distal end 112 further includes a probing tip 114, which is useful for examination and inspection of interior surfaces of a drilled hole in bone, as will be described in FIGS. 3A and 3B.

The device 100 further includes a depth gauge member 116 slidably mounted within the handle 102. The depth gauge member 116 generally includes a hollow elongated body 118 having a distal end 120 configured to extend from, and retract towards, the first end of the handle 102 during use, similar to the bone probe shaft 110, as will be described herein. The hollow elongated body 118 has a lumen in which at least a portion of the bone probe shaft 110 is received such that the bone probe 108 and depth gauge member 116 are independently slidable relative to one another and the handle 102. The device 100 further includes one or more depth measurement sensors 122 configured to generate an electronic signal indicative of a depth of at least the hole, wherein the electronic signal varies in relation to a distance between the first end 104 of the handle 102 and the distal end 120 of the depth gauge member 116, as will be described in greater detail herein.

The bone probe 108 and depth gauge member 116 may each be coupled to separate slider members for allowing a surgeon to manually control movement of the bone probe 108 and depth gauge member 116 independent of one another. For example, as shown in FIG. 1, a first slider 124 may be coupled to at least the bone probe shaft 110 and is slidable along a longitudinal axis of the handle 102, which such movement of the first slider 124 causes corresponding movement of the bone probe shaft 110. Although not shown in FIGS. 1 and 2, a second slider may be coupled to the depth gauge member 116 and is similarly slidable along the longitudinal axis of the handle 102, such that movement of the second slider causes corresponding movement of the depth gauge member 116.

Figure 4A:
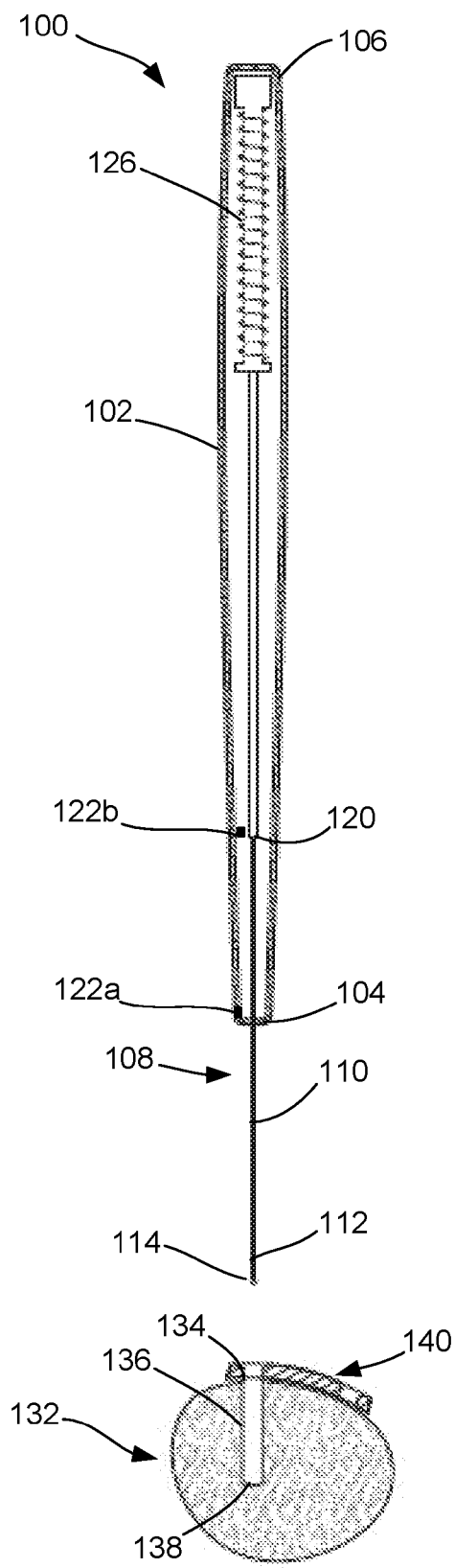
FIGS. 4A and 4B illustrate retraction of the bone probe within the handle member and subsequent compression of a spring assembly upon movement of the handle towards the bone when the probing tip of the distal end of the bone probe shaft is in contact with the bottom of the drilled hole in the bone.
Figure 4B:
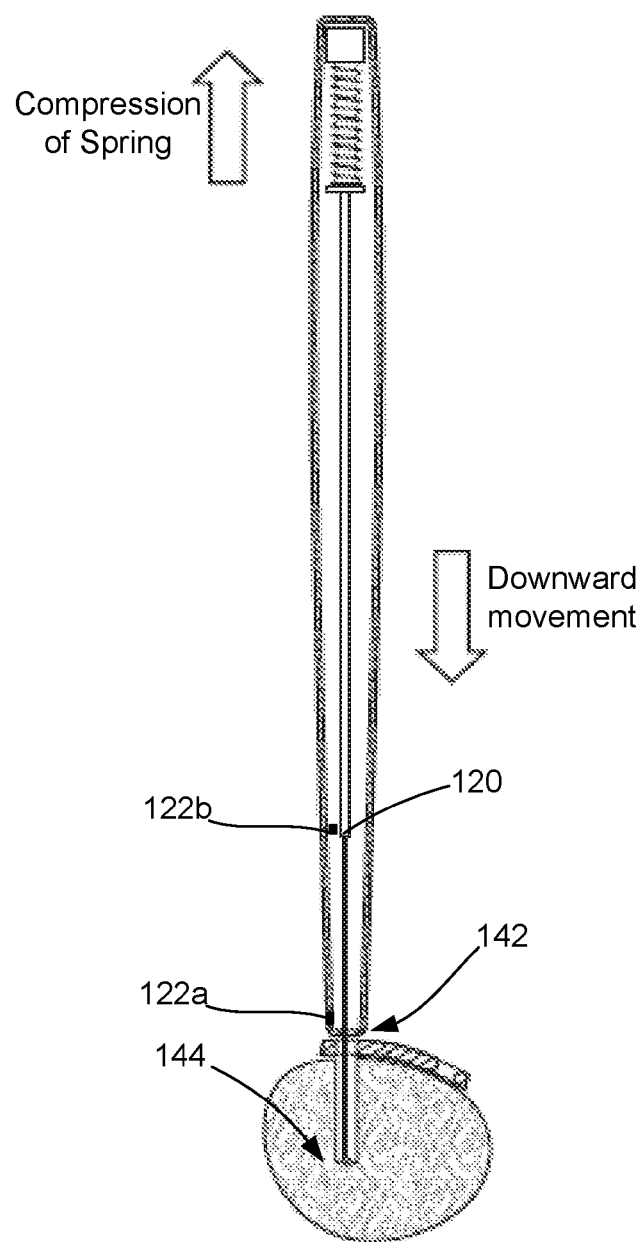

The device 100 may further include a spring assembly 126 coupled to at least one of the bone probe 108 and depth gauge member 116. The spring assembly 126 may be configured to provide a biasing force upon at least one of the bone probe 108 and depth gauge member 116 so as to maintain either the bone probe 108 or depth gauge member 116 in a default extended position. For example, as shown in FIGS. 1 and 2, the bone probe 108 is generally positioned in an extended configuration (probing tip 114 extended out of first end 104 of handle 102), in which a surgeon may now examine an interior surface of a drilled hole, as is shown in FIGS. 4A and 4B.

During a bone-related procedure involving placement of a screw, or other fastener, it may be desirable to determine whether drilling of the hole resulted in any cracks or openings, either along an interior side wall of the hole or at the base of the hole. Ensuring the integrity of the drilled hole is important because unintended cracks, openings, or irregularities can increase the risk that the screw will either not securely attach itself within the hole or may result in chipping or fragmenting of bone during fastening of the screw within the hole. It is generally not possible for a surgeon to visual examine the integrity of the drilled hole due to a limited field of view within the hole (drilled holes can be relatively small in width, such as 5 mm or less in some instances).

The bone probe 108 allows for a surgeon to feel the interior side walls and bottom of a drilled hole so as to locate any cracks or other unintended openings or irregularities along the interior of the hole. For example, probing tip 114 is configured for contacting an interior portion of the hole and at least a portion of the elongated shaft 110 may be substantially flexible or semi-rigid to provide a proper "feel" to the surgeon during examination of the hole in the bone. For example, the shaft 110 of the bone probe 108 may be substantially non-elastic such that the surgeon can apply pressure against the interior wall of the hole to feel for irregularities or the base of the hole via tactile feedback provided by the shaft 110. In some embodiments, the shaft 110 may be tapered such that the shaft narrows in width in a direction towards the probing distal tip. In this manner, the flexibility of the shaft may increase along the shaft in a direction toward the probing tip 114.

Figure 3A:
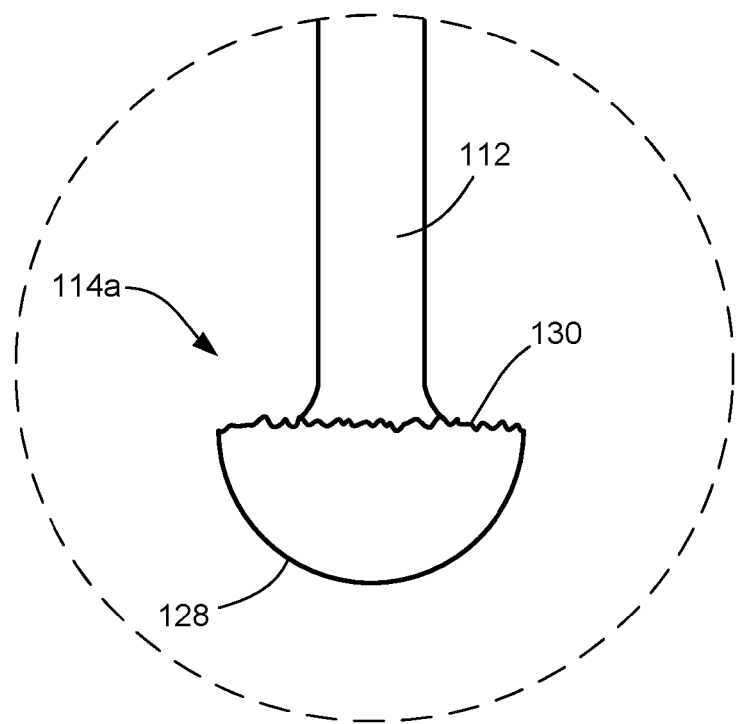
FIGS. 3A and 3B are enlarged front and side views, respectively, of one embodiment of a probing tip defined on the distal end of the bone probe shaft.
Figure 3B:
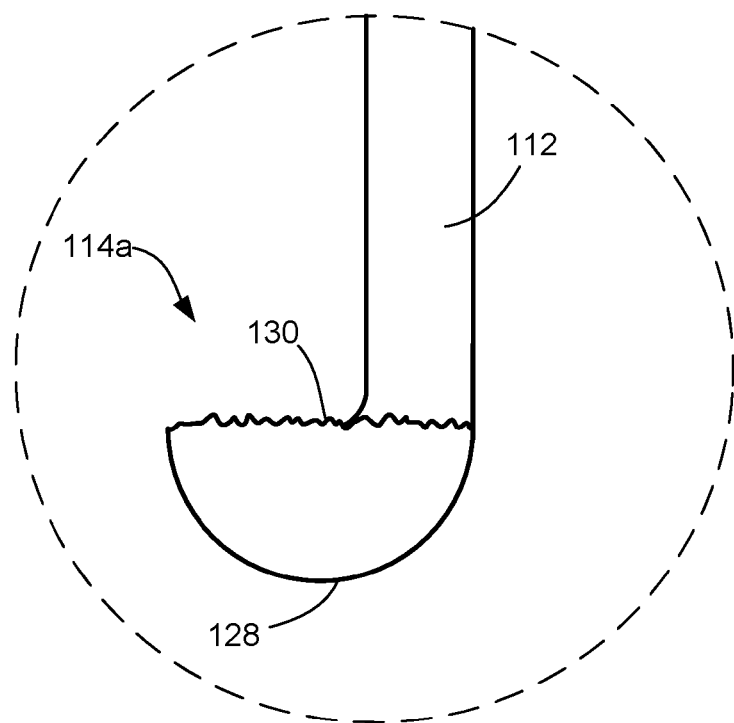

FIGS. 3A and 3B are enlarged front and side views, respectively, of one embodiment of a probing tip 114a defined on the distal end 112 of the bone probe shaft 110. As shown, the probing tip 114a may include an arcuate first portion 128 shaped and configured to contact an interior surface of the hole with little or no resistance and provide tactile feedback of the interior surface to the surgeon. For example, as shown, the first portion 128 is substantially curved or spherical so as to prevent or minimize the risk that the probing tip 114a would penetrate or otherwise engage of portion of the interior surface of the hole. Rather, the first portion 128 is shaped so as to glide or easily slide along the interior surface, while still allowing sufficient contact to provide tactile feedback to the surgeon. Accordingly, the arcuate first portion 128 may lessen or eliminate tissue irritation that may otherwise occur when a sharper object is used to probe the bone opening.

The probing tip 114a further includes a second portion 130 having an engagement surface shaped and configured to establish purchase with a portion of the interior surface of the hole and associated with a bottom of the hole upon sufficient application of force to the shaft. The engagement surface may be a substantially abrupt edge of the probing tip 114, in which the transition between the first portion 128 and second portion 130 is sudden (e.g., sharp corner or edge). Accordingly, upon sufficient pressure, the engagement surface is configured to pierce or establish purchase with tissue in the interior of the hole. Thus, the probing tip 114a is multifunctional in that the first portion 128 allows for probing of the interior surfaces to provide a surgeon with a "feel" for examination purposes and to further locate the bottom of the hole and the second portion 130 allows for the surgeon to establish purchase at the desired site (i.e., the bottom of the hole) so as to stabilize the bone probe in the desired position, at which point, the depth gauge member can be used for measuring the depth of the hole.

In some embodiments, the engagement surface of the second portion 130 may include surface texturing to enhance friction between the engagement surface and a portion of bone. For example, in some procedures in which a plate or implants is to be secured with screws through a bicortical drill hole, the probing tip may extend entirely through the hole (from one side of the bone to the other), at which point the surgeon may pull the bone probe back towards the hole such that the engagement surface of the second portion of the probing tip establishes purchase with one side of the bone, and the surface texturing enhances friction between the engagement surface and bone to reduce risk of slippage.

Figure 3C:
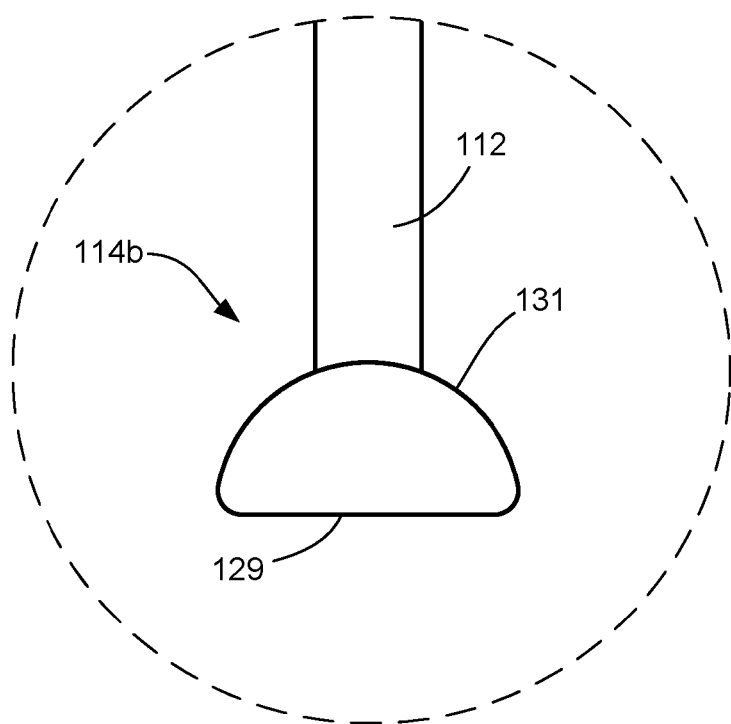
FIGS. 3C and 3D are enlarged front and side views, respectively, of another embodiment of a probing tip defined on the distal end of the bone probe shaft.
Figure 3D:
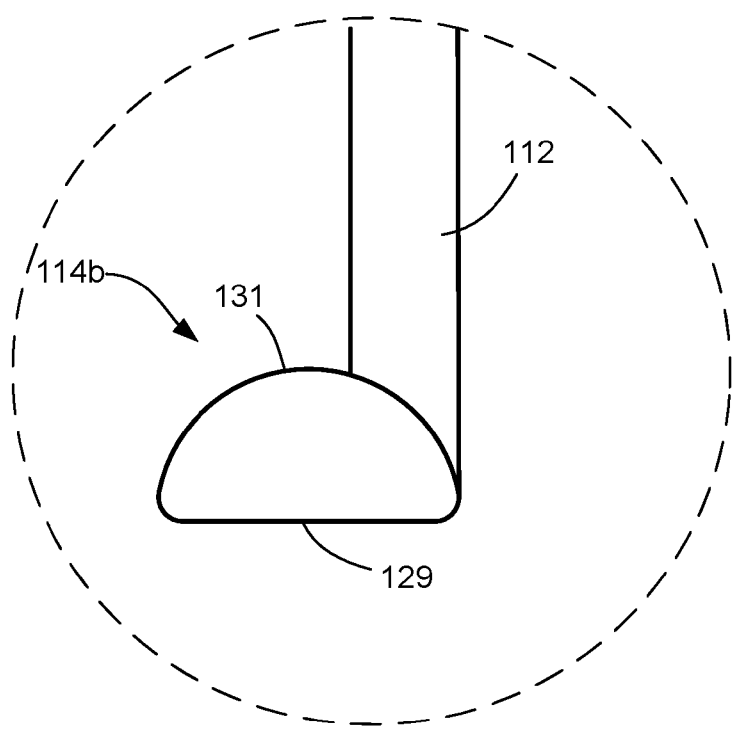

FIGS. 3C and 3D are enlarged front and side views, respectively, of another embodiment of a probing tip 114b defined on the distal end 112 of the bone probe shaft 110. As shown, the probing tip 114b may include a first portion 129 shaped and configured to contact an interior surface of the hole with little or no resistance and provide tactile feedback of the interior surface to the surgeon. For example, as shown, the first portion 129 has a substantially planar or flat surface with rounded edges so as to prevent or minimize the risk that the probing tip 114b would penetrate or otherwise engage of portion of the interior surface of the hole. Rather, the rounded edges of the first portion 129 are shaped so as to glide or easily slide along the interior surface, while still allowing sufficient contact to provide tactile feedback to the surgeon. The substantially planar surface may yield a more accurate depth measurement than a full radius bottom in that, in some circumstances, the flat surface may provide better engagement and sit more flush with the bottom of the hole than the full radius first portion 128 of probing tip 114a (in FIGS. 3A and 3B). It should be noted, however, that the round edges may still provide enough edge to serve as an engagement surface for establishing purchase with a portion of the interior surface of the hole and associated with a bottom of the hole upon sufficient application of force to the shaft. The second portion 131 of probing tip 114b may be substantially curved or spherical.

FIGS. 4A and 4B illustrate an initial process of examining, via the bone probe 108, a drilled hole 134 in a bone 132. For example, as previously described herein, the biasing force from the spring assembly 126 may be sufficient so as to maintain the bone probe 108 in the extended position while the surgeon probes an interior surface 136 of the drilled hole 134 and locates the bottom 138 of the hole 134. However, as shown in FIG. 4B, the biasing force may be overcome upon a surgeon moving the handle 102 in a direction towards the hole 134 once the desired target site is located, such as locating the bottom 138 of the hole 134. The surgeon can move the handle 102 until the first end 104 of the handle 102 abuts either the surface of the bone 132 or a surface of a plate or implant 140, as indicated by arrow 142, thereby resulting in compression of the spring assembly 126 while maintaining placement of the probing tip 114 at the bottom 138 of the hole 134, as indicated by arrow 144. At this point, the depth gauge member 116 can be advanced in a direction towards the hole 134, such that the hollow shaft 118 slides over the bone probe shaft 110, wherein the bone probe shaft 110 generally acts as a guide and holding position as a result of the engagement surface of the second portion 130 of the probing tip 114 having established purchase with the bottom 138 of the hole 134. The depth gauge member 116 can be extended down into the hole 134 until the distal end 120 of the depth gauge member 116 abuts the bottom 138 of the hole 134. Accordingly, the one or more depth measurement sensors 122 can then generate an electronic signal in relation to a distance between the first end 104 of the handle 102 and the distal end 120 of the depth gauge member 116, wherein the electronic signal is indicative of the depth of the hole 134 and the thickness of the plate or implant 140.

The device 100 of the present disclosure may include a variety of different sensing devices suitable for determining a length or depth of the drilled hole or bore to be measured. For example, the one or more depth measurement sensors 122 may include, but are not limited to, an electromechanical or electronic sensor, such as a linear encoder, and may employ any one or more of acoustic, ultrasound, capacitive, electric field, inductive, electromagnetic (e.g., Hall effect-type) and optical components for determining relative or absolute distance measurements. In some embodiments, the sensors 122 may be configured to measure, sense, discriminate, or otherwise determine a length or distance between at least the first end 104 of the handle 102 and the distal end 120 of the depth gauge member 116.

For example, in one embodiment, as shown in FIGS. 4A and 4B, at least a first sensor element 122a is positioned proximate to the first end 104 of the handle 102 and a second sensor element 122b is positioned on the depth gauge shaft 118 proximate the distal end 120. The sensor elements 122a, 122b are configured to measure at least one of relative, absolute and incremental movement (e.g., distance, speed, etc.) of the depth gauge shaft 118 with respect to the first end 104 of the handle 102 during a measurement procedure. For example, in one embodiment, the sensor elements 122a, 122b may be used for measure an absolute distance that the depth gauge 116 distal end 120 is moved relative to the fixed reference point such as, for example the first end 104 of the handle 102.

The first sensor element 122a may be an active inductive, capacitive or optical element that is in communication with circuitry (e.g., a controller) of a user interface portion of the device (e.g., a GUI display or the like with user inputs). The first sensor element 122a may include one or more longitudinally-extending conductors that are wires, cables or traces on a printed circuit board such as, for example, a flex-circuit or the like. Furthermore, the first sensor element 122a may further include a plurality of inductive, capacitive or optical elements that may be coupled with and disposed on the longitudinally-extending conductors. The second sensor element 122b may be configured on the depth gauge shaft 118 in manner so as to cooperate with the first sensor element 122a proximate the first end 104 of the handle 102. For example, the second sensor element 122b may be a generally passive element such as a permanent magnet, optical element (e.g., indicia) or the like that is configured to cooperate, communicate or otherwise interact with the first sensor element 122a. For example, during a measurement procedure, movement of the depth gauge 116 out of the device handle 102 results in interaction between the first and second sensor elements 122a, 122b. In particular, as the depth gauge 116 extends from the device handle 102, the first and second sensor elements 122a, 122b move relative to one another (i.e., second sensor element 122b moves past first sensor element 122a and, in combination with one another, provide signals (e.g., pulses, etc.) to the circuitry, which processes the signals and displays a distance measurement on a display and/or transmits the signals to separate computing devices.

In various embodiments of the present invention, the one or more sensors 122 may be connected with a microprocessor and/or other digital electronic device in order to produce an output for an electronic display, such as a liquid crystal display or light-emitting diode display, and or for wireless/wired transmission of electronic signals, comprising the measurement data, to a wireless compatible computing device. For example, in some embodiments, the microprocessor or other digital electronic device may be connected to a wireless transmitter for wireless transmission of electronic signals. In some embodiments, a signal conditioning circuit may interpose the inductive or capacitive elements of the electronic sensor and the microprocessor or other digital electronic device used to drive the display, thus ensuring that correct input current and voltage levels are provided to the various components. The device may further include a power source, such as a primary or secondary battery, may be connected to the signal conditioning circuit or to the microprocessor directly.

It should be noted that the device 100 of the present disclosure may include a variety of different electronic sensor and circuitry assemblies for determining and transmitting depth measurements, including the sensors and systems discussed in U.S. Pat. Nos.: 7,165,336; 7,444,756; 7,493,703; 7,607,238; 7,676,943; 7,685,735; 7,730,629; 7,895,762; 7,895,767, the contents of each of which are hereby incorporated by reference in their entirety.

Figure 5:
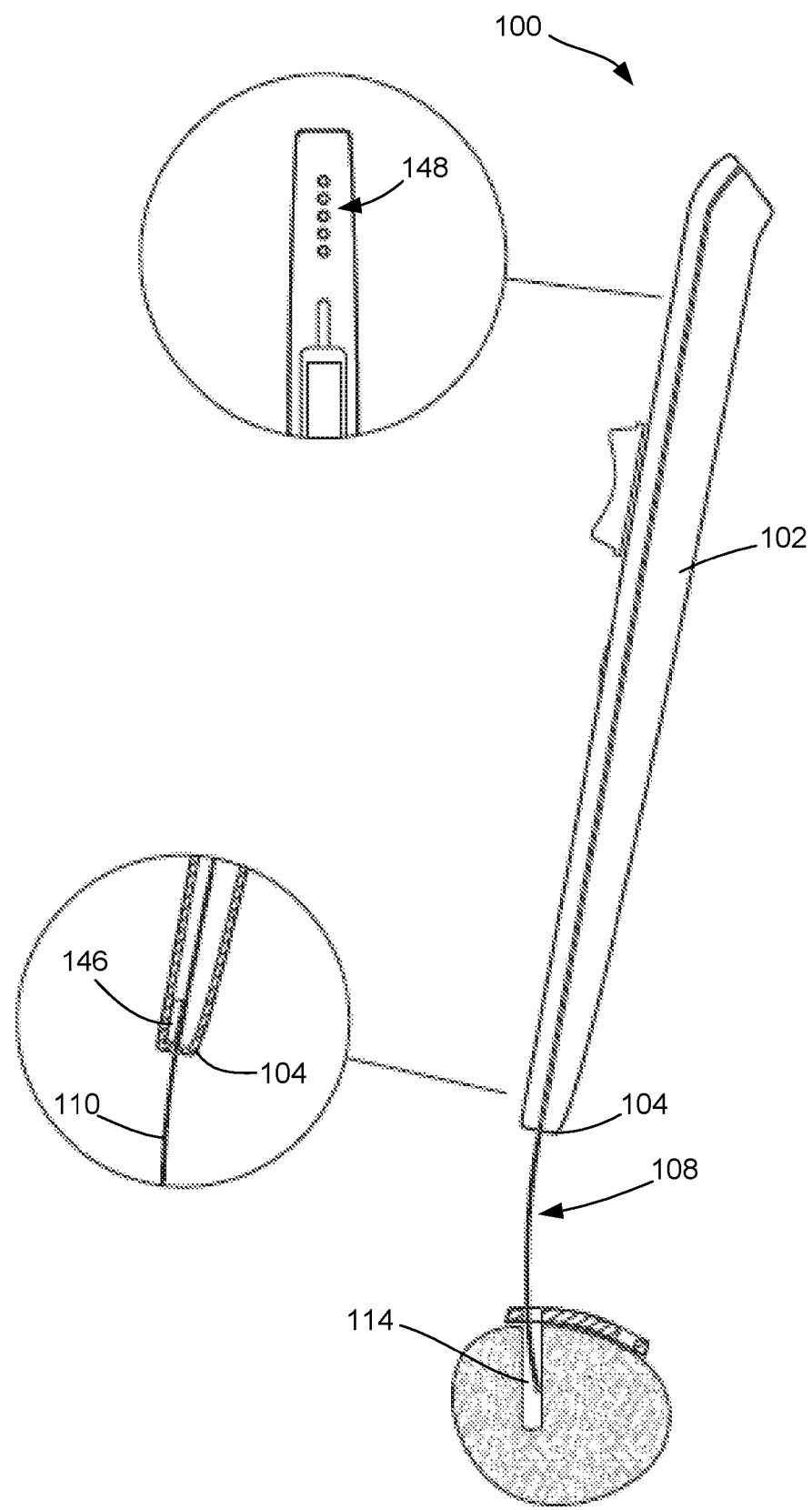
FIG. 5 is a side view of the medical device of FIG. 1 including a strain sensor sensing strain upon the bone probe shaft and providing an electronic signal indicative of the strain to an audio or visual component for providing an audible or visual alert.

FIG. 5 is a side view of the medical device 100 including a strain sensor 146 for sensing strain upon the bone probe shaft 110 as a result of probing the interior surface of a drilled hole. The sensor 146 may include a strain gauge or the like configured to determine a strain of the bone probe shaft 110, which may be useful for alerting the surgeon of an amount of resistance that the distal probing tip 114 is encountering during probing of the interior of the hole. For example, while a surgeon may be able to "feel" the interior surface and further have a sense of when the probing tip 114 actually makes contact with the bottom of the hole, the strain sensor 146 may further generate an electronic signal based on a sensed strain of the shaft 110 which may then be used to provide an audible and/or visual alert, via a device 148 (i.e., speaker or lights) to the surgeon indicating that the probing tip 116 is in fact positioned at the bottom of the hole.

For example, the resistance encountered when the probing tip 116 engages the bottom of the hole may have a certain strain value (i.e., above a certain threshold) which may be different than a resistance encountered with the sidewalls of the hole (which may have a softer, spongier tissue). Accordingly, the audible and/or visual alert may confirm to a surgeon whether they are in fact positioned at the bottom of the hole or if too much pressure is being placed against the interior surface such that they risk possibly inadvertently piercing the interior surface.

Figure 6:
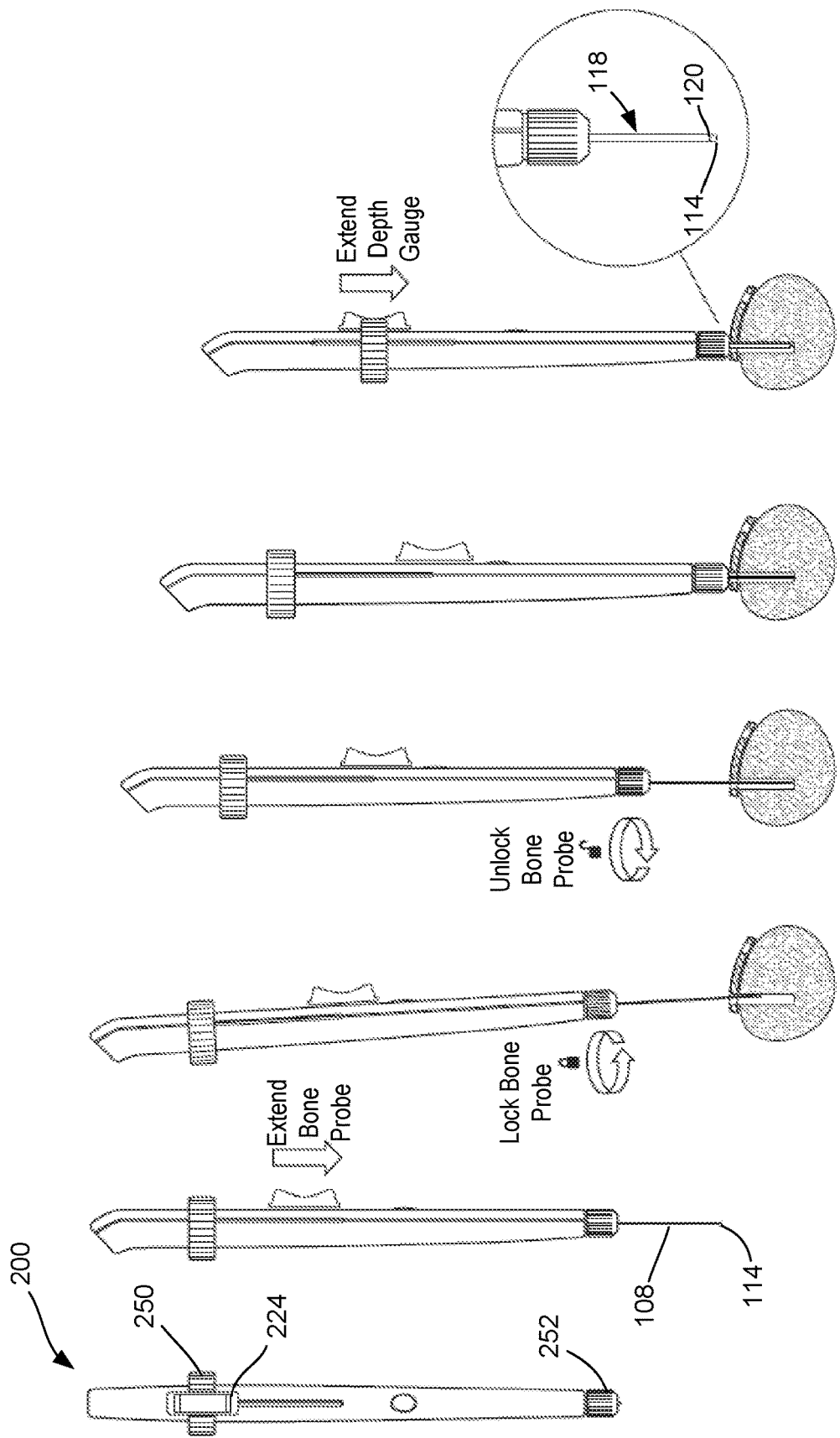
FIGS. 6A-6F illustrate a series of steps for performing a procedure of probing a drilled hole and subsequently obtaining a depth measurement using another embodiment of a medical device consistent with the present disclosure.

FIGS. 6A-6F illustrate a series of steps for performing a procedure of probing a drilled hole and subsequently obtaining a depth measurement using another embodiment of a medical device 200 consistent with the present disclosure. As shown, the device 200 may be similarly configured as device 100 previously described herein. However, as shown in FIG. 6A, both the bone probe 108 and depth gauge member 116 may both be completely withdrawn into the handle 102 until either a first slider 224 is moved, resulting in corresponding movement of the bone probe 108, or a second slider 250 is moved, resulting in corresponding movement of the depth gauge member 116, as shown in FIG. 6E.

In addition to including sliders for allowing independent movement of the bone probe and depth gauge member, the device 200 further includes a locking member 252 for locking a position of at least the bone probe 108. As shown, the locking member 252 is coupled to the first end 104 of the handle 102 and is associated with at least the bone probe 108 in such as manner so as to allow/prevent movement of the bone probe 108. For example, the locking member 252 has an unlocked configuration and a locked configuration, wherein, in the unlocked configuration, the locking member 252 allows the bone probe 108 to freely move and, when in the locked configuration, the locking member 252 prevents movement of the bone probe 108.

For example, upon extending the bone probe 108, a surgeon may then place the locking member 252 in a locked configuration, as shown in FIG. 6C, in which the locking member 252 is configured to provide sufficient contact with the bone probe shaft 110 so as to prevent, or make difficult, the movement of the bone probe shaft 110 relative to the first end 104 of the handle 102, thereby providing an amount of rigidity to the probe shaft 110. Accordingly, a surgeon may now perform examination of a drilled hole without concern of the bone probe 108 withdrawing back into the handle 102 or being loose.

Upon locating the base or bottom of the hole, the surgeon may then apply sufficient force upon the bone probe shaft 110 so that the engagement surface of the second portion of the probing tip engages and establishes purchase with the bottom of the hole, or a sidewall immediately adjacent to the bottom, as shown in FIG. 6D. Upon establishing engagement, the surgeon may then place the locking member 252 in an unlocked configuration, now that the bone probe shaft 110 is in a stabilized in position. The surgeon may then move the handle in a directions towards the bone until the first end of the handle abuts the surface of the bone or the surface of the plate/implant, as shown in FIG. 6E, at which point, the depth gauge member 116 can be used for measuring the depth of the hole. As shown in FIG. 6F, the surgeon may then advance the depth gauge member 116 towards hole, via the second slider 250, such that the distal end 120 of the depth gauge member shaft 118 extends from the first end of the device handle and advances into the hole, sliding over the bone probe 108. While the bone probe 108 is maintained in engagement with the bottom of the hole via the probing tip, the depth gauge member may be advanced in a direction towards the bottom of the hole until the distal end of the depth gauge member makes contact with the bottom of the hole. The bone probe essentially acts as a guide upon which the depth gauge member slide over when advancing to the bottom of the hole.

The sensor is configured to generate an electronic signal based on a distance between the first end of the body and the distal end of the depth gauge member, wherein the electronic signal is indicative of at least a depth of the hole. In particular, the sensor may include inductive or capacitive elements or assemblies configured to sense the location of the distal end of the depth gauge member relative to the first end of the device body, and, as a result, generate an electronic signal representing the distance there between. Accordingly, the sensed distance between the first end of the device handle (when abutting the bone surface) and the distal end of the depth gauge member (when abutting the bottom of the hole) is the depth of the hole.

It should be noted that the device may include logic or allow for adjustment to the sensing capabilities so as to program the sensor to account for other variables when sensing the depth of the hole. For example, in some embodiments, certain procedures require fixing a plate or implant to the bone via screws. Accordingly, the screw length must not only be sufficient to fill the hole but also long enough to account for the thickness of a plate or implant through which it passes when engaging the hole. Accordingly, in some embodiments, the sensor may be programmed so as to account for the thickness of the plate or implant and will further include that thickness in the electronic signal produced, such that the electronic signal is indicative of the total depth that a corresponding screw length will need to cover, including the depth of the hole in the bone in addition to the thickness of the plate or implant through which the screw will pass through and the screw head will engage.

Furthermore, in some instances, first end of the device handle will be directly abutting a surface of the plate or implant, as shown in FIG. 6F, which is directly abutting the surface of the bone, when the surgeon is measuring the depth. Thus, in this case, the sensor is still able to sense a distance between the first end of the device handle and the distal end of the depth gauge member, which will provide an overall depth, rather than just a depth of the hole in the bone.

Figure 7:
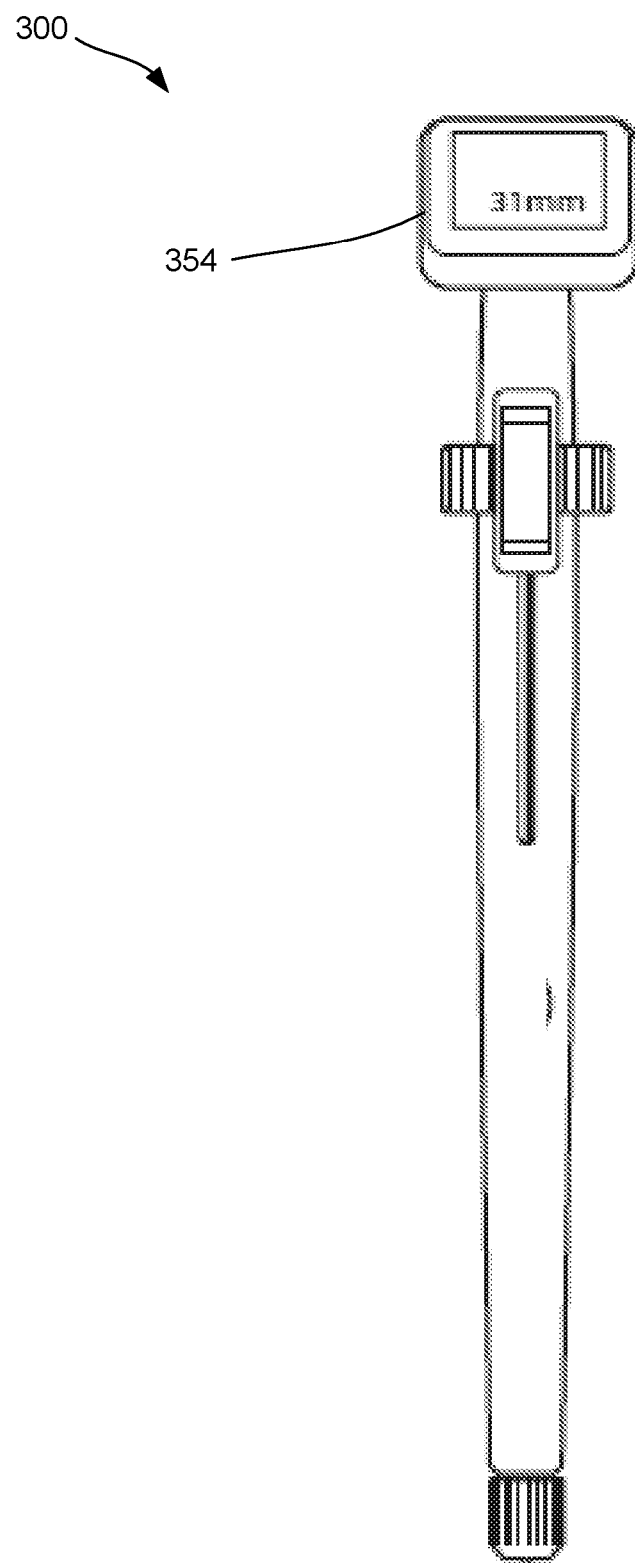
FIG. 7 is another embodiment of a medical device consistent with the present disclosure having a display for providing a digital readout of a depth measurement of the hole.

FIG. 7 is another embodiment of a medical device 300 consistent with the present disclosure having a display 354 for providing a digital readout of a depth measurement of the hole based on the electronic signal from the sensor. The display 354 may include a liquid crystal display or an LED display, for example.

Figure 8:
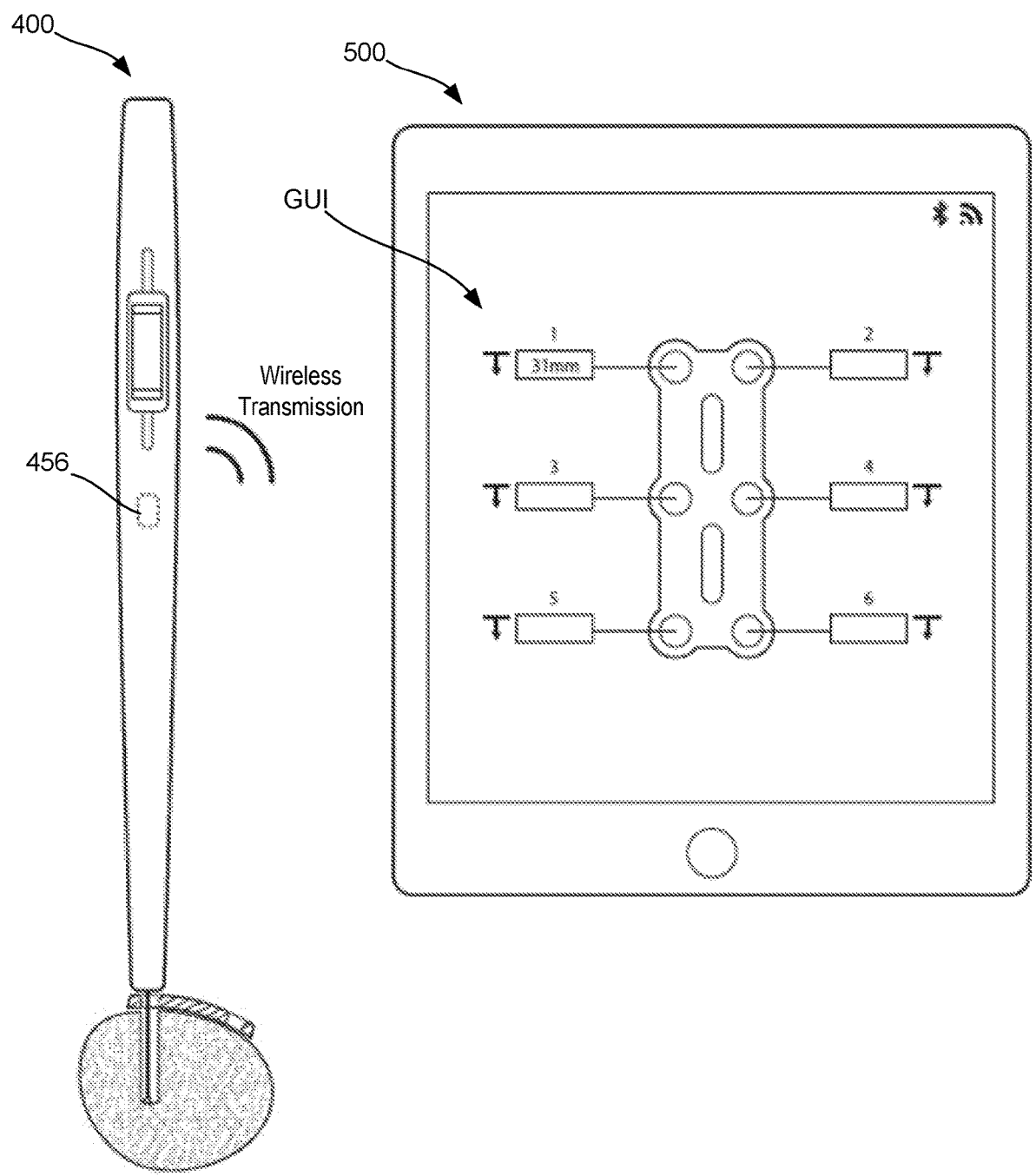
FIG. 8 is another embodiment of a medical device consistent with the present disclosure configured to wirelessly communicate with and transmit depth measurement data to a wireless computing device to record, store, and/or visually display measured depths.

FIG. 8 is another embodiment of a medical device 400 consistent with the present disclosure configured to wirelessly communicate with and transmit depth measurement data to a wireless computing device 500 over a network, to record, store, and/or visually display measured depths based on electronic signals from the sensor for determining depth of drilled holes. For example, the device 400 may include a wireless transmitter 456 configured to wireless communicate and exchange information, including the electronic signal, with a wireless display or computing device 500 for at least visually providing a depth measurement of the hole based on the electronic signal from the sensor. The separate display or computing device 500 may include, but is not limited to, a monitor or panel display, a PC, a notebook, a tablet computer, a smartphone, or other computing device configured to wirelessly communicate with the wireless transmitter 456.

The network may be any network that carries data. Non-limiting examples of suitable networks that may be used as network include WiFi wireless data communication technology, the internet, private networks, virtual private networks (VPN), public switch telephone networks (PSTN), integrated services digital networks (ISDN), digital subscriber link networks (DSL), various second generation (2G), third generation (3G), fourth generation (4G) cellular-based data communication technologies, Bluetooth radio, Near Field Communication (NFC), the most recently published versions of IEEE 802.11 transmission protocol standards, other networks capable of carrying data, and combinations thereof.

Furthermore, in some embodiments, the computing device 500 may include a specific software application that may be directed to maintaining a record of the hole measurements and/or provide an interactive user interface (GUI) in which multiple holes can be mapped to a particular plate or implant and the depth of each hole (including the thickness of the plate or implant) can be included and stored for records.

Figure 9:
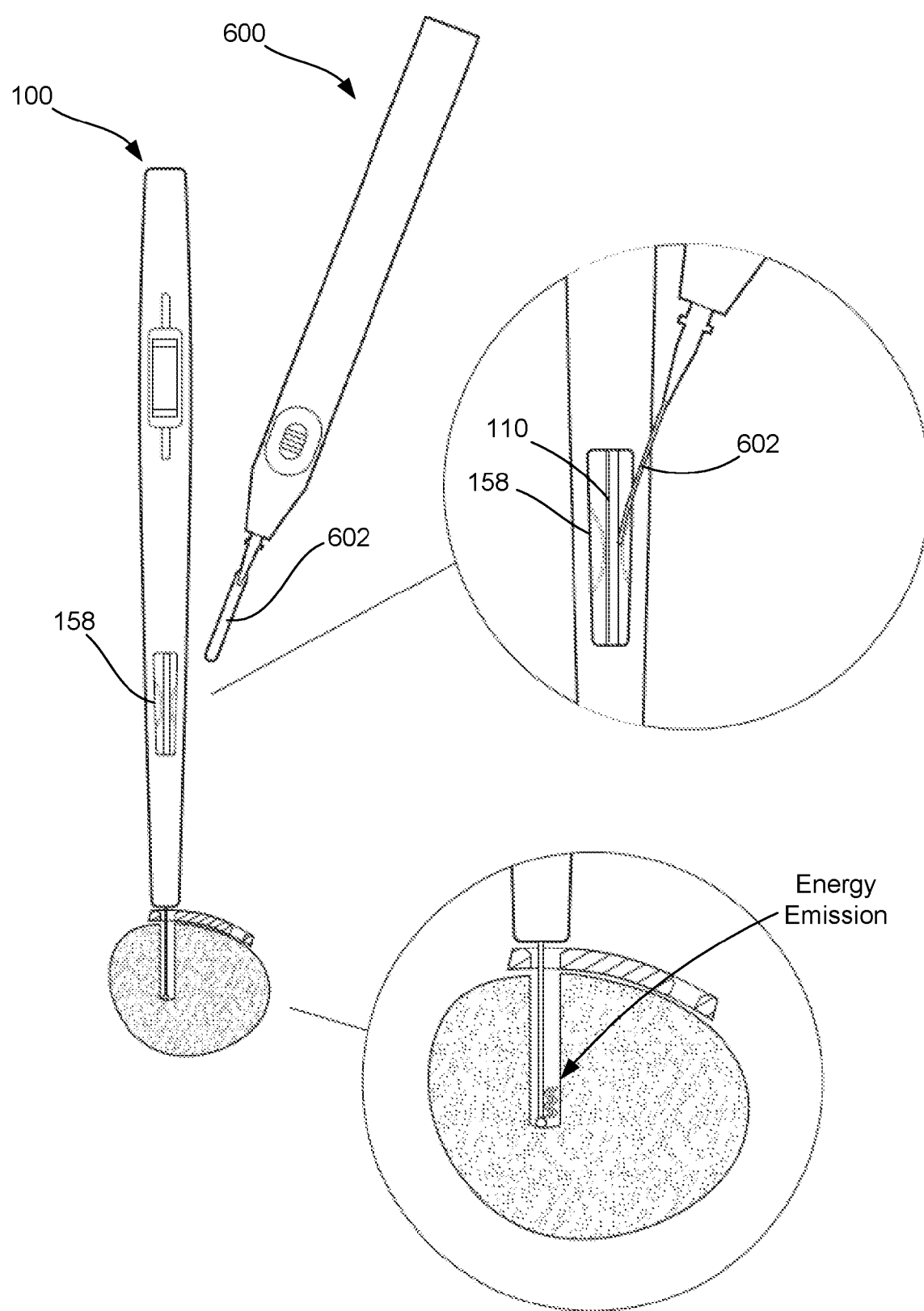
FIGS. 9 and 10 illustrate the compatibility of a medical device of the present disclosure with other medical devices so as to provide additional features, in additional bone probing and depth measurement, such as energy emission (FIG. 9) and sensing capabilities (FIG. 10)
Figure 10:
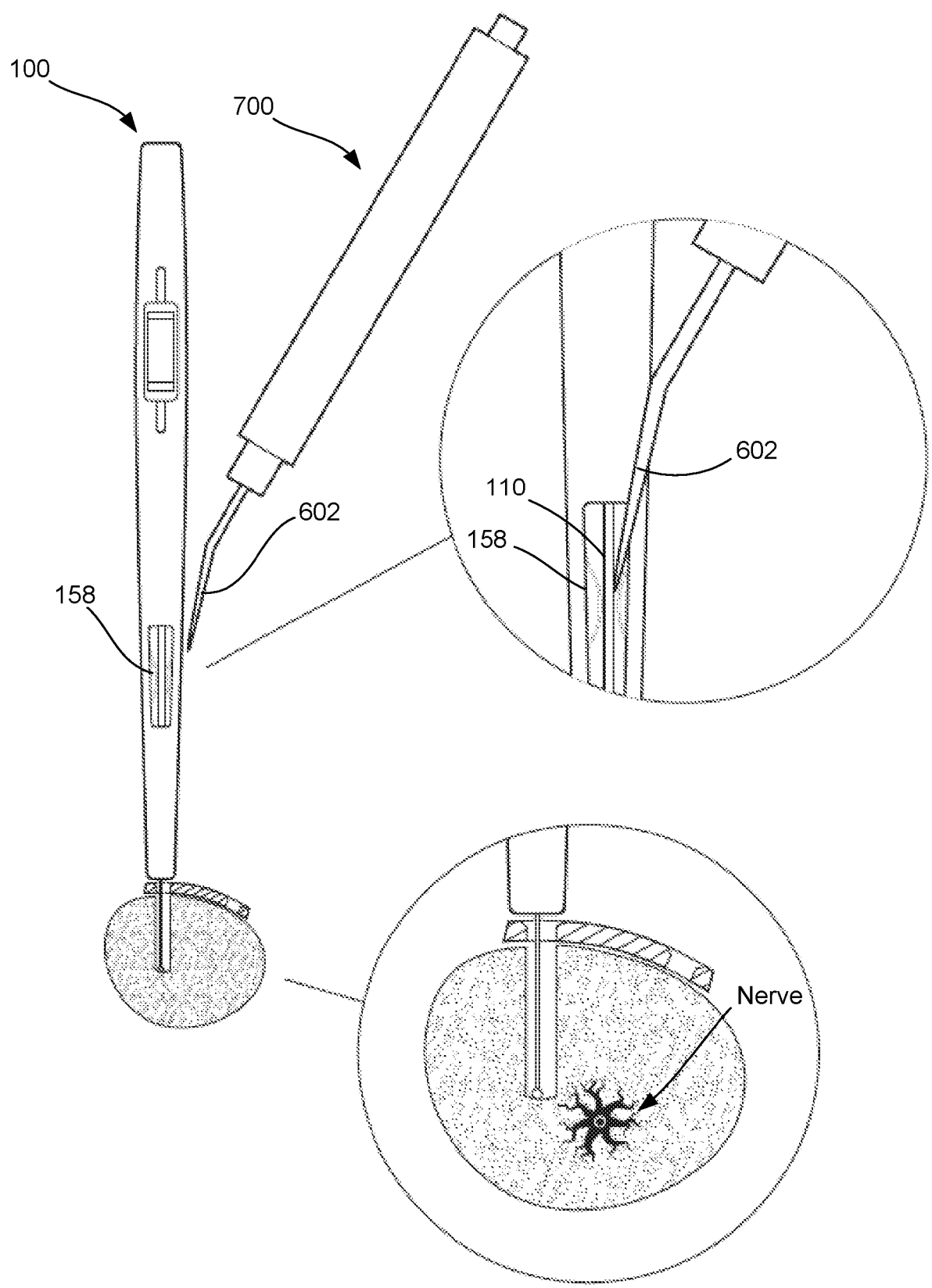

FIGS. 9 and 10 illustrate the compatibility of a medical device of the present disclosure with other medical devices so as to provide additional features, in additional bone probing and depth measurement, such as energy emission (FIG. 9) and sensing capabilities (FIG. 10). For example, in some embodiments, the bone probe shaft 110 may include an electrically conductive material (e.g., a metal such as stainless steel, nitinol, or aluminum), wherein a portion of the bone probe shaft 110 may be exposed, or otherwise accessible, along a portion of the device handle. In particular, the device handle may include an access region 158 that may be in the form of an aperture, window, or the like, that provides access to an interior of the handle, particularly providing access to an exposed portion of the bone probe shaft. Thus, in some embodiments, an electrical current from a separate device 600, 700 may be supplied to the bone probe shaft via the access region 158 (e.g., slide a working tip of an electrocautery device 600 into the access region 158 to make contact with bone probe shaft 110). Accordingly, as a result of being made from a conductive material, the bone probe shaft 110 may carry the electrical current to the distal probe tip, which may then be used to deliver energy to a desired target (e.g., interior surface of hole of the bone) as a result of the electrical current applied thereto. Similarly, a separate nerve sensing/stimulation device 700 (shown in FIG. 10) may be coupled to the conductive bone probe shaft via the access region, such that the distal probe tip essentially acts as an extension to the nerve sensing/stimulation device and may be used to sense/stimulate nerves within the bone. The separate sensing/nerve stimulation device or system 700 may include, for example, existing capital equipment or a handheld battery-powered neuromonitoring device.

Figure 11:
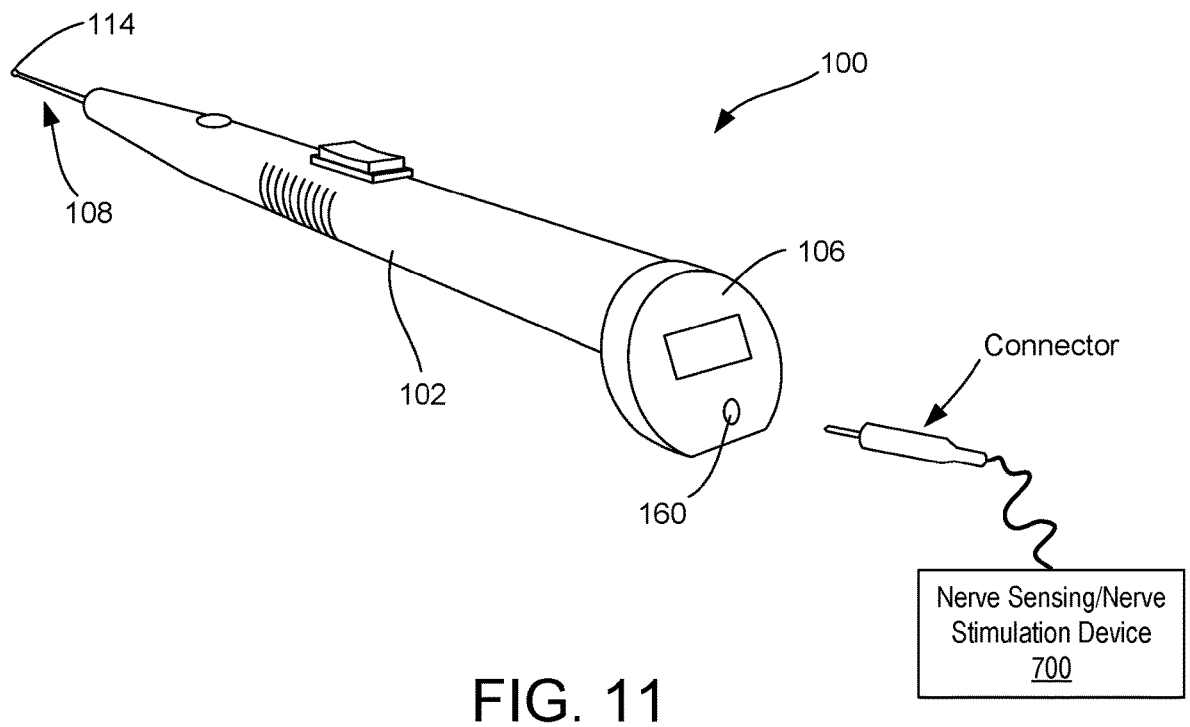
FIG. 11 is a perspective view of a medical device consistent with the present disclosure and having a neuromonitoring port configured to receive a corresponding input connector from a nerve sensing/nerve stimulation device and provide an electrical pathway to the bone probe.

FIG. 11 is a perspective view of a medical device 100 having a port 160 provided on the proximal, or second end 106, of the device body 102. The port 160 is configured to receive a corresponding input connector from a nerve sensing/nerve stimulation device 700. The port 160 (hereinafter referred to as "neuromonitoring port 160") is coupled to the bone probe shaft 108 and is configured to provide an electrical pathway from the nerve sensing/nerve stimulation device 700 to the bone probe 108 upon insertion of the input connector into the neuromonitoring port 160. As previously described, the bone probe shaft 110 may include an electrically conductive material (e.g., a metal such as stainless steel, nitinol, or aluminum) and thus may carry an electrical signal. Thus, in some embodiments, an electrical signal from the nerve sensing/nerve stimulation device 700 may be supplied to the bone probe shaft 110 via the neuromonitoring port 160. Accordingly, as a result of being made from a conductive material, the bone probe shaft 110 may carry the electrical signal to the distal probe tip 114, which may then be used to sense/stimulate nerves adjacent or in close proximity to the drilled hole in the bone, either when the bone probe 108 is directly placed within the drilled hole or when the bone probe 108 is in contact with a screw placed within the drilled hole.

Figure 12:
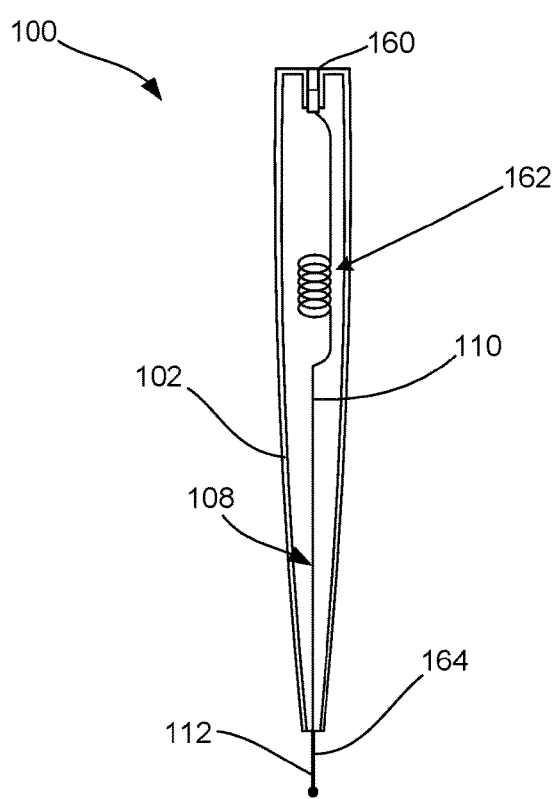
FIG. 12 is a side view, partly in section, of the medical device of FIG. 11 illustrating the configuration of the bone probe shaft to carry electrical signals to and from the nerve sensing/nerve stimulation device.

FIG. 12 is a side view, partly in section, of the medical device 100 of FIG. 11 illustrating the configuration of the bone probe shaft 110 for carrying electrical signals to and from the nerve sensing/nerve stimulation device. Upon insertion of the electrical connector into the neuromonitoring port 160, a pathway is provided between the nerve sensing/nerve stimulation device 700 and the bone probe 108. The bone probe shaft 108 generally includes a soft coil portion 162 configured to allow conduction of an electrical signal provided by the nerve sensing/stimulation device 700 while the shaft 110 moves between fully retracted and fully extended positions and intermediate positions there between, particularly when measuring the depth of the drilled hole 134. In some embodiments, a portion of the distal end 112 of the bone probe 108, particularly the exposed portion of the shaft 110 extendable outside of device body 102 may include an insulating material 164, while the distal probing tip 114 is free of insulating material.

Figure 13A:
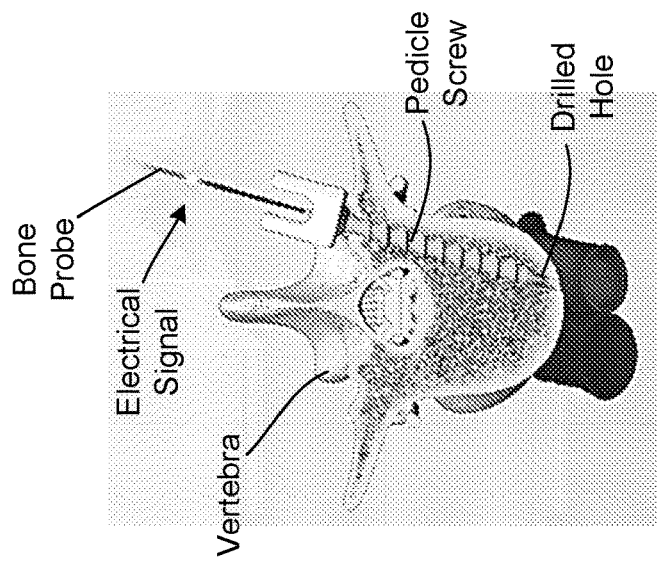
FIGS. 13A, 13B, and 13C illustrate the transmission of a signal from bone probe to a screw positioned within a hole in a vertebra for neuromonitoring capabilities.
Figure 13B:
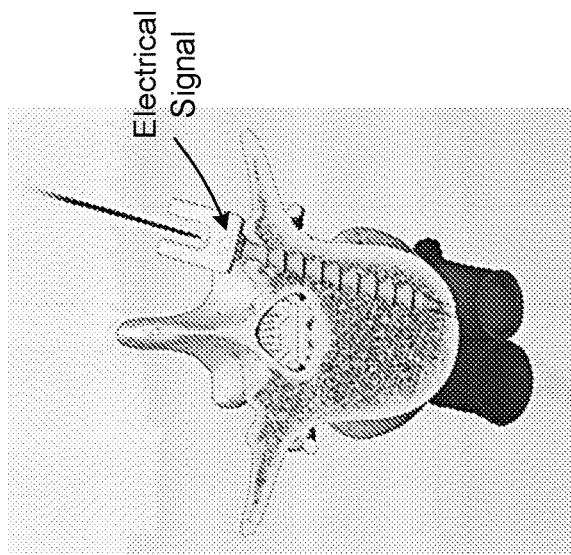
Figure 13C:
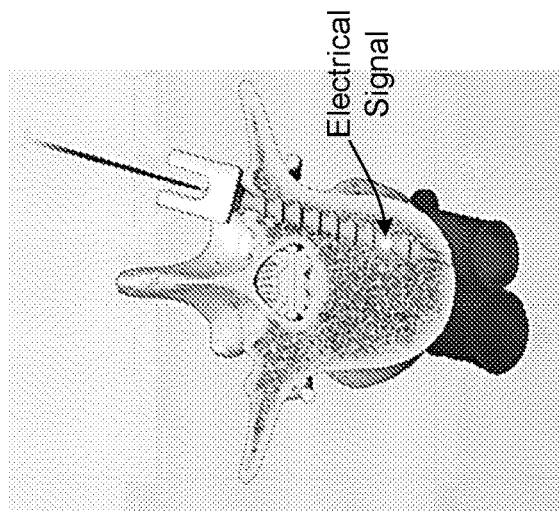

FIGS. 13A, 13B, and 13C illustrate the transmission of a signal from bone probe 108 to a screw positioned within a hole in a vertebra for neuromonitoring capabilities, particularly useful during an open spinal procedure. As shown in FIG. 13A, upon coupling the nerve sensing/nerve stimulation device 700 to the medical device 100 (e.g., inserting the electrical connector into the neuromonitoring port 160), a surgeon can begin a neuromonitoring procedure to determine whether there are any critical neurological structures adjacent to or within an unsafe proximity to the drilled hole and screw. In particular, a surgeon can perform neuromonitoring procedure by placing the bone probe 108 directly within the drilled hole prior to screw placement, in which the distal probing tip 114 can be placed in direct contact with the interior of the hole and transmit the electrical signal from the nerve sensing/nerve stimulation device 700 to the bone tissue and will subsequently receive a response signal to then be carried back to the nerve sensing/nerve stimulation device 700 for processing. In another method, as shown in FIGS. 13A, 13B, and 13C, the surgeon is performing the neuromonitoring procedure once the screw is already in place (e.g., already fitted within the drilled hole) by placing the distal probing tip 114 in direct contact with the screw, which, in turn, will act as a conduit and carry electrical signals to and from the distal probing tip 114 and the nerve sensing/nerve stimulation device 700.

Accordingly, the medical device consistent with the present disclosure is a three-in-one single use device designed to more accurately and safely measure the screw hole pathway. For example, the probing tip of the bone probe provides a user (e.g., surgeon) with superior tactile feedback to assist the surgeon in confirming a safe pathway within the bone. The electronic measurement/digital sensing is designed to provide more accurate depth measurement for the screw pathway. The neuromonitoring feature is used to stimulate the pathway and/or screw, ensuring the screw is safely positioned away from any critical neurological structures. Overall, the medical device of the present disclosure is a faster, safer, more accurate and user-friendly solution for surgeons when placing bone screws, particularly pedicle screws during spinal fusion surgery, thereby minimizing spine surgery complications and reducing overall healthcare costs.

Figure 14:
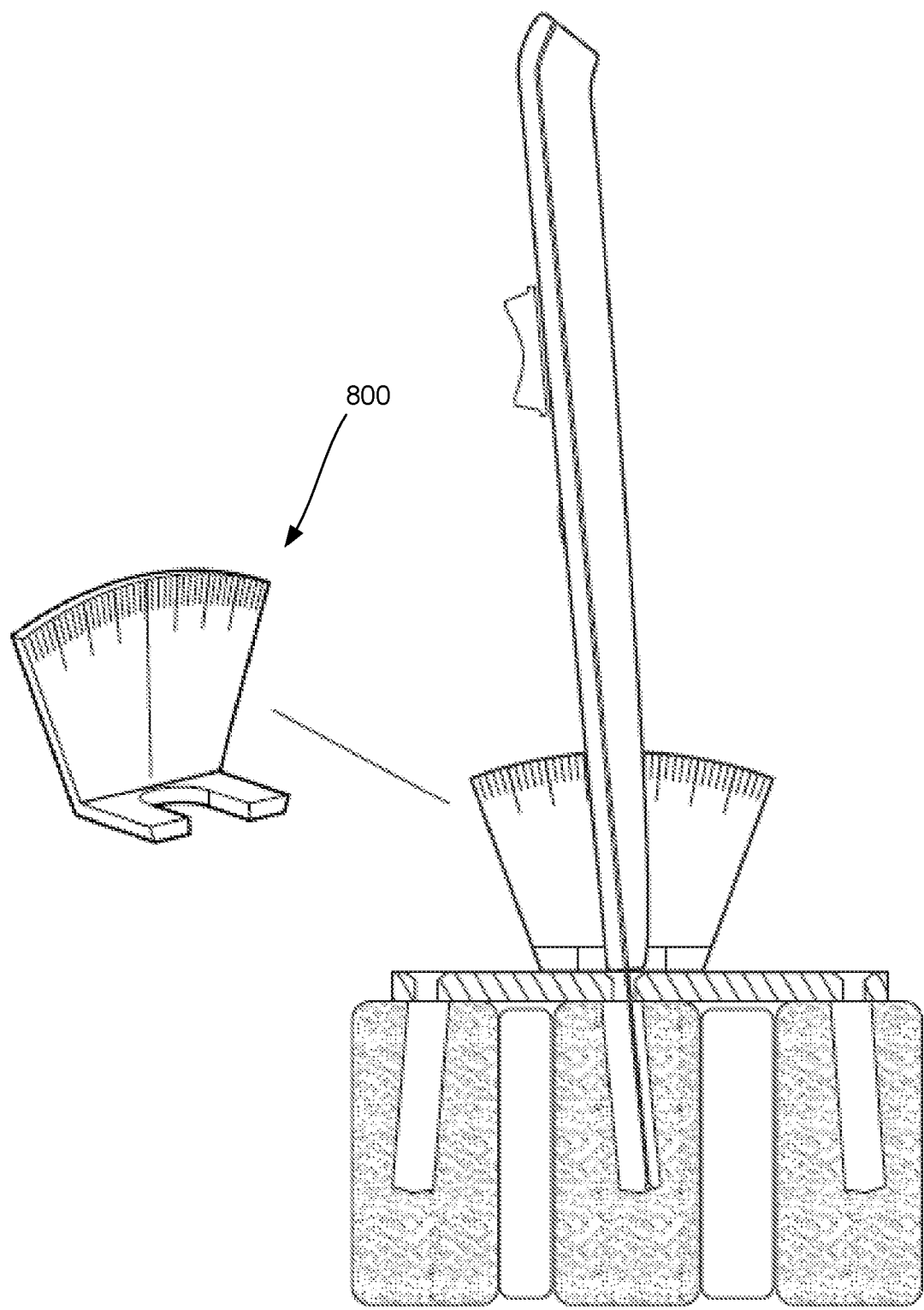
FIG. 14 illustrates an angle guide for use with the medical device of the present disclosure.

FIG. 14 illustrates an angle guide 800 for use with the medical device of the present disclosure. In some instances, holes may be drilled into bone at an angle. Accordingly, the angle guide may be useful in providing a surgeon with a visual guide as to the correct angle at which to position the device when attempting to examine the hole and further locate the bottom of the hole to carry out the depth measurements.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A device for examination and measurement of a bore hole formed in a bone, the device comprising:
    a handle;
    a bone probe slidably disposed with respect to the handle and comprising a shaft including a distal end including an engagement surface shaped and configured to establish purchase with a portion of an interior surface of the bore hole and associated with a bottom of the bore hole upon sufficient application of force to the shaft;
    a depth gauge member slidably disposed with respect to the handle and comprising a hollow elongate body including a distal end, the hollow elongated body including a lumen in which at least a portion of the bone probe shaft is received such that the bone probe and depth gauge member are independently slidable relative to one another; and
    a sensor configured to generate an electronic signal indicative of a depth of the bore hole, wherein the electronic signal varies in relation to a distance between the handle and the distal end of the elongate body of the depth gauge member.

2. The device of claim 1 wherein the distal end of the bone probe comprises a substantially arcuate shape.

3. The device of claim 1 wherein the distal end of the bone probe comprises a substantially planar surface.

4. The device of claim 3 further comprising an alert device for receiving the electronic signal indicative of strain from the sensor and output at least one of an audible alert or a visual alert providing an indication to a user of the degree of strain upon the bone probe shaft.

5. The device of claim 1 wherein the distal end of the bone probe includes surface texturing.

6. The device of claim 1 wherein the sensor is an electrical resistance-based sensor.

7. The device of claim 1 further comprising a display on the handle configured to visually provide a digital readout of a depth measurement of the hole based on the electronic signal from the sensor.

8. The device of claim 7 wherein the display is a liquid crystal display or an LED display.

9. The device of claim 1 further comprising a first slider coupled to the bone probe shaft and slidable along a longitudinal axis of the handle, wherein movement of the first slider causes corresponding movement of the bone probe shaft.

10. The device of claim 9 further comprising a second slider coupled to the depth gauge member and slidable along the longitudinal axis of the handle, wherein movement of the second slider causes corresponding movement of the depth gauge member.

11. The device of claim 1 wherein the handle includes a locking member associated with at least the bone probe, the locking member having an unlocked configuration and a locked configuration.

12. The device of claim 11 wherein the locking member, when in the unlocked configuration, allows the bone probe shaft to move relative to the handle.

13. The device of claim 11 wherein the locking member, when in the locked configuration, provides sufficient contact with the bone probe shaft to prevent, or make difficult, movement of the bone probe shaft relative to the handle.

14. The device of claim 1 further comprising a sensor configured to generate an electronic signal indicative of strain of the bone probe shaft.

15. The device of claim 1 further comprising a wireless transmitter/receiver configured to wirelessly communicate and exchange information, including the electronic signal, with a wireless display or computing device for at least visually providing a depth measurement of the bore hole based on the electronic signal from the sensor.

16. The device of claim 1 wherein the handle comprises a port in communication with a portion of the bone probe shaft and provides access from an exterior of the handle to an interior of the handle and to the bone probe shaft.

17. The device of claim 16 wherein the bone probe shaft comprises an electrically conductive material.

18. The device of claim 17 wherein the port is configured to receive and place an input connector of a second medical device into electrical communication with the bone probe shaft, wherein the bone probe shaft is configured to carry electrical signals to and from the input connector of the second medical device.

19. The device of claim 18 wherein the second medical device comprises a neuromonitoring device.

20. The device of claim 19 wherein the distal end of the bone probe is configured to provide signals to the neuromonitoring device indicative of whether a nerve is present within or adjacent to the bore hole.

* * * * *